US012582407B2

(12) United States Patent
  Damato

(10) Patent No.: US 12,582,407 B2
(45) Date of Patent: Mar. 24, 2026

(54) DEVICES AND METHODS FOR APPLYING A HEMOSTATIC CLIP ASSEMBLY

(71) Applicant: Conmed Corporation, Largo, FL (US)

(72) Inventor: Daniel P. Damato, Boston, MA (US)

(73) Assignee: Conmed Corporation, Largo, FL (US)

( * ) Notice: Subject to any disclaimer, the term of this patent is extended or adjusted under 35 U.S.C. 154(b) by 365 days.

(21) Appl. No.: 18/030,766

(22) PCT Filed: Apr. 30, 2021

(86) PCT No.: PCT/US2021/030246
  § 371 (c)(1),
  (2) Date: Apr. 6, 2023

(87) PCT Pub. No.: WO2022/076032
  PCT Pub. Date: Apr. 14, 2022

(65) Prior Publication Data
  US 2023/0404593 A1    Dec. 21, 2023

Related U.S. Application Data

(60) Provisional application No. 63/091,349, filed on Oct. 14, 2020, provisional application No. 63/089,097, filed on Oct. 8, 2020.

(51) Int. Cl.
  *A61B 17/128*      (2006.01)
  *A61B 17/00*       (2006.01)
  (Continued)

(52) U.S. Cl.
  CPC .... *A61B 17/1285* (2013.01); *A61B 17/00234* (2013.01); *A61B 17/122* (2013.01);
  (Continued)

(58) Field of Classification Search
  None
  See application file for complete search history.

(56) References Cited

U.S. PATENT DOCUMENTS

| | | | |
|---|---|---|---|
| 4,651,737 A | 3/1987 | Deniega | |
| 5,626,607 A | 5/1997 | Malecki et al. | |

(Continued)

FOREIGN PATENT DOCUMENTS

| | | |
|---|---|---|
| CN | 102727276 A | 10/2012 |
| CN | 203539404 U | 4/2014 |

(Continued)

OTHER PUBLICATIONS

International Search Report and Written Opinion, of the European Patent Office, dated Sep. 30, 2021, in corresponding International Patent Application PCT/US2021/030246.

(Continued)

*Primary Examiner* — Shaun L David
(74) *Attorney, Agent, or Firm* — Troutman Pepper Locke LLP; Scott D. Wofsy; Michael J. Pollack

(57) ABSTRACT

A device for applying a hemostatic clip assembly includes a proximal delivery catheter having a proximal handle assembly, a catheter body defining a longitudinal axis and extending distally from the proximal handle assembly, and a distal clip assembly removably connected to a distal end of the catheter body. The distal clip assembly includes a distal clip housing, a jaw assembly and a jaw adapter yoke. The jaw assembly has a pair of cooperating jaw members fixed to the distal clip housing by a first pin oriented orthogonally relative to the longitudinal axis. The jaw member is configured to rotate about the first pin and about the longitudinal axis. Each jaw member includes a proximal body portion and a distal end effector, wherein the proximal body portion includes a respective cam slot and a rear opening connected to the cam slot and defining at least one proximal cantilever jaw arm.

22 Claims, 23 Drawing Sheets

(51) Int. Cl.
    *A61B 17/122*        (2006.01)
    *A61B 17/29*         (2006.01)
(52) U.S. Cl.
    CPC .................. *A61B 2017/003* (2013.01); *A61B*
         *2017/00473* (2013.01); *A61B 2017/00477*
         (2013.01); *A61B 2017/2936* (2013.01)

(56)            References Cited

U.S. PATENT DOCUMENTS

| | | | |
|---|---|---|---|
| 5,749,881 A | 5/1998 | Sackier et al. |
| 5,766,184 A | 6/1998 | Matsuno et al. |
| 5,766,189 A | 6/1998 | Matsuno |
| 6,464,710 B1 | 10/2002 | Foster |
| 7,094,245 B2 | 8/2006 | Adams et al. |
| 7,452,327 B2 | 11/2008 | Durgin et al. |
| 7,494,461 B2 | 2/2009 | Wells et al. |
| 7,879,052 B2 | 2/2011 | Adams et al. |
| 8,083,668 B2 | 12/2011 | Durgin et al. |
| 8,088,061 B2 | 1/2012 | Wells et al. |
| 8,162,959 B2 | 4/2012 | Cohen et al. |
| 8,444,660 B2 | 5/2013 | Adams et al. |
| 8,545,519 B2 | 10/2013 | Aguirre et al. |
| 8,551,119 B2 | 10/2013 | Kogiso et al. |
| 8,663,247 B2 | 3/2014 | Menn et al. |
| 8,685,048 B2 | 4/2014 | Adams et al. |
| 8,709,027 B2 | 4/2014 | Adams et al. |
| 8,771,293 B2 | 7/2014 | Surti et al. |
| 8,845,658 B2 | 9/2014 | Adams |
| 8,858,588 B2 | 10/2014 | Sigmon, Jr. et al. |
| 8,915,837 B2 | 12/2014 | Wells et al. |
| 8,939,997 B2 | 1/2015 | Martinez et al. |
| 8,974,371 B2 | 3/2015 | Durgin et al. |
| 8,979,891 B2 | 3/2015 | McLawhorn et al. |
| 9,271,731 B2 | 3/2016 | Adams et al. |
| 9,332,988 B2 | 5/2016 | Adams et al. |
| 9,339,270 B2 | 5/2016 | Martinez et al. |
| 9,370,371 B2 | 6/2016 | Durgin et al. |
| 9,375,219 B2 | 6/2016 | Surti et al. |
| 9,445,821 B2 | 9/2016 | Wells et al. |
| 9,480,478 B2 | 11/2016 | Adams |
| 9,743,933 B2 | 8/2017 | Phillips-Hungerford et al. |
| 9,775,590 B2 | 10/2017 | Ryan et al. |
| 9,795,390 B2 * | 10/2017 | Jin .................... A61B 17/1285 |
| 9,895,154 B2 | 2/2018 | Cohen et al. |
| 9,955,977 B2 | 5/2018 | Martinez et al. |
| 9,980,725 B2 | 5/2018 | Durgin et al. |
| 9,987,018 B2 | 6/2018 | Surti et al. |
| 10,010,336 B2 | 7/2018 | Martinez et al. |
| 10,143,479 B2 | 12/2018 | Adams et al. |
| 10,154,842 B2 | 12/2018 | Wells et al. |
| 10,166,028 B2 | 1/2019 | Menn et al. |
| 10,172,623 B2 | 1/2019 | Adams et al. |
| 10,172,624 B2 | 1/2019 | Adams et al. |
| 10,307,169 B2 | 6/2019 | Wells et al. |
| 10,335,159 B2 | 7/2019 | Naveed et al. |
| 10,537,314 B2 | 1/2020 | Ryan et al. |
| 10,548,612 B2 | 2/2020 | Martinez et al. |
| 10,575,857 B2 | 3/2020 | King et al. |
| 10,588,635 B2 | 3/2020 | Smith et al. |
| 10,595,877 B2 | 3/2020 | Menn et al. |
| 10,624,642 B2 | 4/2020 | Randhawa |
| 10,646,230 B2 | 5/2020 | Phillips-Hungerford et al. |
| 10,786,254 B2 | 9/2020 | Wells et al. |
| 10,792,046 B2 | 10/2020 | Martinez et al. |
| 10,813,650 B2 | 10/2020 | Surti et al. |
| 10,820,904 B2 | 11/2020 | Ryan et al. |
| 10,835,261 B2 | 11/2020 | Menn et al. |
| 10,905,434 B2 | 2/2021 | Estevez et al. |
| 10,952,725 B2 | 3/2021 | Durgin et al. |
| 10,952,742 B2 | 3/2021 | Lehtinen et al. |
| 10,952,743 B2 | 3/2021 | Adams et al. |
| 11,020,125 B2 | 6/2021 | Randhawa et al. |
| 11,045,194 B2 | 6/2021 | King et al. |
| 11,071,552 B2 | 7/2021 | Saenz Villalobos et al. |
| 11,083,465 B2 | 8/2021 | Ryan et al. |
| 11,129,623 B2 | 9/2021 | Saenz Villalobos et al. |
| 11,129,624 B2 | 9/2021 | Martinez et al. |
| 11,202,637 B2 | 12/2021 | Murray et al. |
| 11,253,259 B2 | 2/2022 | Smith et al. |
| 11,399,835 B2 | 8/2022 | Congdon et al. |
| 11,426,177 B2 | 8/2022 | Congdon et al. |
| 2002/0045909 A1 | 4/2002 | Kimura et al. |
| 2006/0155308 A1 | 7/2006 | Griego |
| 2008/0208217 A1 | 8/2008 | Adams |
| 2008/0306491 A1 | 12/2008 | Cohen et al. |
| 2010/0268254 A1 | 10/2010 | Golden et al. |
| 2012/0065646 A1 | 3/2012 | Phillips-Hungerford et al. |
| 2014/0249551 A1 | 9/2014 | Adams et al. |
| 2014/0257342 A1 | 9/2014 | Adams et al. |
| 2014/0364874 A1 | 12/2014 | Adams |
| 2016/0128698 A1 | 5/2016 | Adams et al. |
| 2016/0143644 A1 | 5/2016 | Adams et al. |
| 2016/0213378 A1 | 7/2016 | Adams et al. |
| 2016/0220260 A1 | 8/2016 | Martinez et al. |
| 2017/0325823 A1 | 11/2017 | Phillips-Hungerford et al. |
| 2018/0049745 A1 | 2/2018 | Randhawa et al. |
| 2018/0085122 A1 | 3/2018 | Ryan et al. |
| 2018/0125497 A1 | 5/2018 | Cohen et al. |
| 2018/0193021 A1 | 7/2018 | Martinez et al. |
| 2018/0235608 A1 | 8/2018 | Durgin et al. |
| 2019/0053804 A1 | 2/2019 | Wells et al. |
| 2019/0059905 A1 | 2/2019 | Adams et al. |
| 2019/0083099 A1 | 3/2019 | Adams et al. |
| 2019/0083100 A1 | 3/2019 | Menn et al. |
| 2019/0090883 A1 | 3/2019 | Adams et al. |
| 2019/0150929 A1 | 5/2019 | Gregan et al. |
| 2019/0223875 A1 | 7/2019 | Saenz Villalobos et al. |
| 2019/0247049 A1 | 8/2019 | Wells et al. |
| 2019/0336130 A1 * | 11/2019 | He ..................... A61B 17/083 |
| 2020/0100791 A1 * | 4/2020 | Tsuchiya .............. A61B 17/122 |
| 2020/0138444 A1 | 5/2020 | Martinez et al. |
| 2020/0146686 A1 * | 5/2020 | Haack ................ A61B 17/1285 |
| 2020/0163676 A1 | 5/2020 | Menn et al. |
| 2020/0214707 A1 | 7/2020 | Randhawa |
| 2021/0022747 A1 | 1/2021 | Menn et al. |
| 2021/0137525 A1 * | 5/2021 | Yu ..................... A61B 17/128 |
| 2022/0160366 A1 * | 5/2022 | Kuhn .................. A61B 17/122 |
| 2022/0175386 A1 | 6/2022 | Martinez et al. |

FOREIGN PATENT DOCUMENTS

| | | |
|---|---|---|
| CN | 104248461 A | 12/2014 |
| CN | 104546055 A | 4/2015 |
| CN | 204364061 U | 6/2015 |
| CN | 107684448 A | 2/2018 |
| CN | 109009310 A | 12/2018 |
| CN | 110141295 A | 8/2019 |
| CN | 209884245 U | 1/2020 |
| EP | 3476307 A1 | 5/2019 |
| EP | 3643255 A1 | 4/2020 |
| EP | 3763298 A1 | 1/2021 |
| WO | 9915089 A1 | 4/1999 |
| WO | 2015176361 A1 | 11/2015 |
| WO | 2016184120 A1 | 11/2016 |
| WO | 2020186838 A1 | 9/2020 |
| WO | 2021/087461 A2 | 5/2021 |
| WO | 2021/087464 A2 | 5/2021 |
| WO | 2022/076032 A1 | 4/2022 |
| WO | 2022/076033 A1 | 4/2022 |
| WO | 2022/260751 A1 | 12/2022 |

OTHER PUBLICATIONS

International Search Report and Written Opinion, of the European Patent Office, dated Oct. 11, 2021, in corresponding International Patent Application PCT/US2021/030263.
International Search Report and Written Opinion for PCT Application No. PCT/US2020/058553, dated May 3, 2021.
International Search Report and Written Opinion for PCT Application No. PCT/US2020/058556, dated Jul. 9, 2021.

(56)　　　　　References Cited

OTHER PUBLICATIONS

International Search Report and Written Opinion for PCT Application No. PCT/US2022/024654, dated Sep. 20, 2022.

* cited by examiner

*Fig. 6*
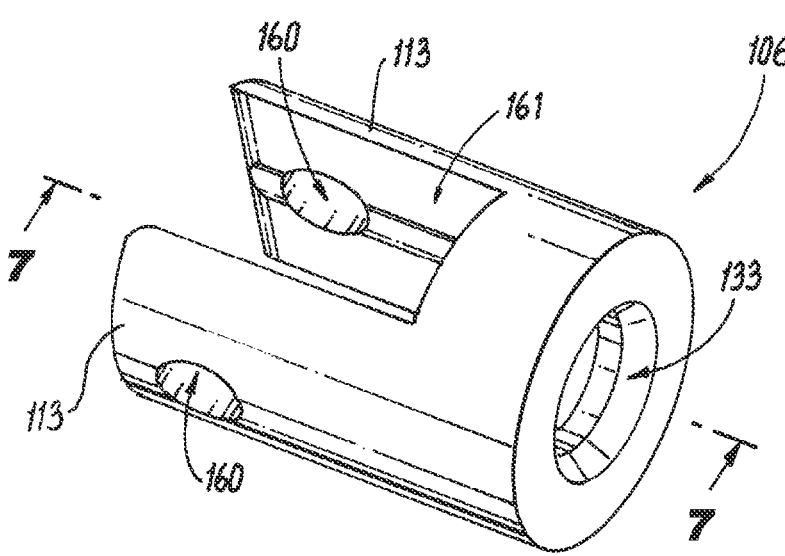
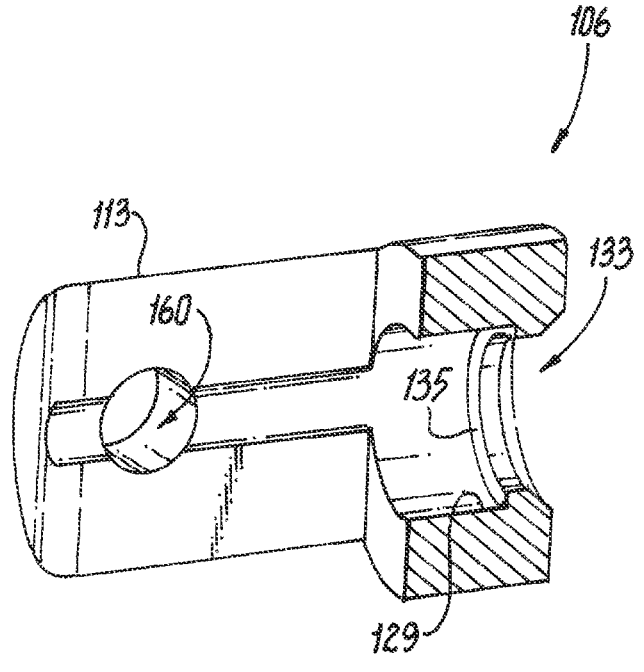
*Fig. 7*

DEVICES AND METHODS FOR APPLYING A HEMOSTATIC CLIP ASSEMBLY

CROSS-REFERENCE TO RELATED APPLICATIONS

This application is a U.S. National Stage filed under 35 U.S.C. § 371, based on International PCT Application No. PCT/US2021/030246, filed on Apr. 30, 2021, which claims the benefit of priority to U.S. Provisional Patent Application Ser. No. 63/089,097, filed Oct. 8, 2020, and U.S. Provisional Patent Application Ser. No. 63/091,349 filed Oct. 14, 2020, the disclosures of which are herein incorporated by reference in their entirety.

BACKGROUND OF THE INVENTION

1. Field of the Invention

The subject invention is directed to surgical equipment, and more particularly to hemostatic clips used endoscopic surgical procedures.

2. Description of Related Art

Endoscopic or "minimally invasive" hemostatic clips are used in performance of hemostasis to stop and prevent re-bleeding, or in procedures such as ampullectomy, polypectomy, tissue repair and correction of other tissue defects. Such procedures are typically performed by grasping the tissue with the hemostatic clip. Benefits of using hemostatic clips in such procedures include reduced trauma to the patient, low re-bleeding rate, reduced opportunity for infection, and decreased recovery time.

The subject invention provides an improved mechanism for a hemostatic clip. The novel design allows for a shorter deployed clip body, improved tissue grasping and clip locking, and an improved disconnecting feature, which are described in detail herein below, along with other novel devices and systems.

SUMMARY OF THE DISCLOSURE

The subject invention is directed to a new and useful surgical device for applying a hemostatic clip assembly. The device includes a proximal delivery catheter having a proximal handle assembly and an elongated catheter body extending distally from the proximal handle assembly. The elongated catheter body defines a longitudinal axis. The device includes a distal clip assembly removably connected to a distal end of the elongated catheter body. The distal clip assembly includes a distal clip housing, a jaw adapter yoke slidably positioned within the distal clip assembly, and a jaw assembly. The jaw assembly has a pair of cooperating jaw members fixed to the jaw adapter yoke by a first pin. The first pin is oriented orthogonally relative to the longitudinal axis. The proximal delivery catheter is configured and adapted to transmit linear motion along the longitudinal axis and torsion about the longitudinal axis to at least a portion of the distal clip assembly. At least one of the jaw members is configured and adapted to rotate about the first pin and rotate about the longitudinal axis.

In accordance with some embodiments, the distal clip housing includes a pair of spaced apart arms defining a slot configured and adapted to provide clearance for respective proximal portions of the jaw members to rotate relative the first pin. The distal clip assembly can include a second pin connecting between the jaw members and the distal clip housing. Each jaw member can include a proximal body portion and a distal end effector. The proximal body portion of each jaw member can include a respective cam slot configured and adapted to receive the second pin and a pivot aperture configured and adapted to receive the first pin.

The cam slots are configured and adapted to translate along the second pin to move axially relative to the distal clip housing to move the jaw members between the open configuration, where respective distal tips of the jaw members are moved away from one another, the closed configuration where the respective distal tips of the jaw members are approximated towards one another to grasp tissue, and a locked configuration.

In some embodiments, each cam slot defines a distal portion and a proximal portion with a middle portion therebetween. The middle portion of each cam slot is angled relative to the proximal and distal portions of each cam slot. The proximal portion of each cam slot can define a proximal axis extending in a first direction. The middle portion of each cam slot can define a middle axis extending at an oblique angle relative to the proximal axis. Each cam slot can include a distal locking neck projecting into the cam slot defining a distal locking area. The jaw members can be in the locked configuration when the second pin is distal relative to the distal locking neck in the distal locking area. The distal locking neck can include at least one of a protrusion projecting into the cam slot or a tapered portion. The tapered portion can have a narrower effective width than the remainder of the cam slot at a given point.

The jaw adapter yoke can include a proximal receiving portion and the proximal delivery catheter includes a spring release having a distal portion configured and adapted to be received within the proximal receiving portion of the jaw adapter yoke to transmit axial and rotational force to the jaw adapter yoke. A portion of the spring release between a terminal distal end of the spring release and the outwardly extending flange portion can be a constant diameter. The proximal delivery catheter can include a drive wire coupled to a proximal portion of the spring release to transmit linear and rotational motion from the drive wire to the jaw adapter yoke. The proximal handle assembly can include an actuation portion coupled to a proximal end of the drive wire, and a grasping portion, wherein the actuation portion is configured and adapted to translate relative to the grasping portion to apply axial force to the drive wire.

In certain embodiments, the proximal delivery catheter includes a spring tube between a proximal end of the distal clip assembly and a distal end of the catheter body. The spring tube can include at least one cantilever arm removably coupled to the distal clip housing. The at least one cantilever arm can include an inwardly extending flange that removably engages with a circumferential slot defined about a periphery of a proximal end of the distal clip housing. The proximal delivery catheter can include a spring release positioned at least partially within the spring tube. The spring tube can include an inward projection. The spring release can include an outwardly extending flange portion configured and adapted to interact with the inward projection of the spring tube to selectively deflect the at least one cantilever arm of the spring tube and release the inwardly extending flange of the at least one cantilever arm from the circumferential slot of the distal clip housing.

The spring release can include a distal portion configured and adapted to be received within a receiving portion of the jaw adapter yoke to transmit linear and rotational motion to the jaw adapter yoke. The distal portion of the spring release can be divided into at least two tines. Each tine can have a mating surface selectively engageable with an inner surface of the receiving portion of the jaw adapter yoke. Each tine can be configured and adapted to deflect inwardly and release from the receiving portion when an axial force in a proximal direction is applied to the spring release.

In accordance with another aspect, a device for applying a hemostatic clip assembly includes a proximal delivery catheter including a proximal handle assembly and an elongated catheter body extending distally from the proximal handle assembly. The proximal delivery catheter includes a spring tube positioned at a distal end of the elongated catheter body, a drive wire movably positioned within the elongated catheter body, and a spring release coupled to a distal end of the drive wire, the elongated catheter body defining a longitudinal axis. The spring tube includes an inward projection and the spring release includes an outwardly extending flange portion configured and adapted to interact with the inward projection of the spring tube. A portion of the spring release between a terminal distal end of the spring release and the outwardly extending flange portion is a constant diameter. The device includes a distal clip assembly removably connected to a distal end of the elongated catheter body. The proximal delivery catheter is configured and adapted to transmit linear motion along the longitudinal axis and torsion about the longitudinal axis to at least a portion of the distal clip assembly.

The distal clip assembly can include a distal clip housing, a jaw adapter yoke slidably positioned within the distal clip assembly, and a jaw assembly having a pair of cooperating jaw members fixed to the jaw adapter yoke by a first pin. The first pin can be oriented orthogonally relative to the longitudinal axis. A proximal body portion of each jaw member can include a respective cam slot, like cam slots described above. The distal clip housing can include a pair of spaced apart arms, like those described above. The distal clip assembly can include a second pin like that described above. Each cam slot can include a distal locking neck projecting into the cam slot defining a distal locking area, similar to the distal locking neck and distal locking area described above. Each cam slot can define a distal portion and a proximal portion, with a middle portion therebetween, as previously described. The proximal handle assembly can include an actuation portion and a grasping portion, as described above.

In accordance with another aspect, a method for firing a hemostatic clip assembly includes positioning a distal clip assembly proximate to, e.g., near, a target location and translating an actuation portion of a proximal handle assembly of a proximal delivery catheter relative to a grasping portion of the proximal handle assembly in at least one of a proximal direction or a distal direction. The distal clip assembly includes a distal clip housing, a jaw adapter yoke slidably positioned within the distal clip assembly, and a jaw assembly having a pair of cooperating jaw members fixed to the jaw adapter yoke by a first pin. The proximal delivery catheter includes an elongated catheter body extending distally from the proximal handle assembly. The elongated catheter body defining a longitudinal axis. The actuation portion is operatively connected to the jaw adapter yoke via a drive wire and a spring release to transmit linear motion along the longitudinal axis and torsion about the longitudinal axis to the jaw adapter yoke. The linear motion of the jaw adapter yoke transmits a linear component of motion to at least one jaw member and a cam slot of at least one jaw member to translate the cam slot along a second pin connecting between at least one of the jaw members and the distal clip housing, thereby rotating at least one of the jaw members about the first pin and to rotate about the longitudinal axis.

Translating the actuation portion can include translating the actuation portion in the proximal direction to transmit the linear motion in the proximal direction to the cam slot to lock the second pin behind a lock protrusion of the cam slot to lock at least one of the jaw members in a locked configuration. Translating the actuation portion can include translating the actuation portion further in the proximal direction to transmit further linear motion in the proximal direction to the spring release. The further linear motion in a proximal direction can de-couple a distal portion of the spring release from a receiving portion of the jaw adapter yoke. Each jaw member can include two proximal cantilever jaw arms. Translating the actuation portion in the proximal direction to transmit the linear motion in the proximal direction to the second pin can include deflecting a first one of the cantilever jaw arms to an angle between 0 and 20 degrees relative to a second one of the cantilever jaw arms such that, in the locked configuration, an angular distance between respective distal tips of the jaw members and the longitudinal axis ranges from 0 to 20 degrees.

In some embodiments, translating the actuation portion includes translating the spring release in the proximal direction causing abutting between an inner diameter surface of at least one cantilever arm of a spring tube with an outwardly extending flange portion of the spring release. The spring tube can be coupled to a proximal end of the distal clip housing via the at least one cantilever arm. In certain embodiments, the abutting causes the at least one cantilever arm to deflect radially outward and disengage from the proximal end of the distal clip housing.

In accordance with another aspect, a hemostatic clip assembly includes a distal clip housing defining a longitudinal axis, a jaw adapter yoke slidably positioned within the distal clip housing, a jaw assembly having a pair of cooperating jaw members fixed to the jaw adapter yoke by a first pin. The jaw adapter yoke is configured and adapted to translate axially along the longitudinal axis and rotate about the longitudinal axis. At least one of the jaw members is configured and adapted to rotate about the first pin and to rotate about the longitudinal axis.

The distal clip housing can include a pair of spaced apart arms, similar to those described above. The hemostatic clip assembly can include a second pin, similar to that described above. Each jaw member and its respective cam slot can be similar to those described above. A first one of the cantilever jaw arms can be configured and adapted to deflect to an angle between 0 and 20 degrees relative to a second one of the cantilever jaw arms such that, in the locked configuration, an angular distance between respective distal tips of the jaw members and the longitudinal axis ranges from 0 to 20 degrees.

In accordance with another aspect, a device for applying a hemostatic clip assembly includes a proximal delivery catheter having a proximal handle assembly and an elongated catheter body extending distally from the proximal handle assembly. The elongated catheter body defines a longitudinal axis. The device includes a distal clip assembly removably connected to a distal end of the elongated catheter body. The distal clip assembly includes a distal clip housing, a jaw assembly and a jaw adapter yoke. The jaw assembly has a pair of cooperating jaw members fixed to the distal clip housing by a first pin. The first pin is oriented orthogonally relative to the longitudinal axis. The jaw adapter yoke is operatively connected to the jaw members.

The proximal delivery catheter is configured and adapted to transmit linear motion along the longitudinal axis and torsion about the longitudinal axis to at least a portion of the distal clip assembly. At least one of the jaw members is configured and adapted to rotate about the first pin and to rotate about the longitudinal axis. Each jaw member includes a proximal body portion and a distal end effector. The proximal body portion of each jaw member includes a respective cam slot and a rear opening connected to the cam slot and defining at least one proximal cantilever jaw arm.

In accordance with some embodiments, the distal clip housing includes a pair of spaced apart arms defining a slot configured and adapted to provide clearance for respective proximal portions of the jaw members to rotate relative the first pin. The distal clip assembly can include a second pin connecting between the jaw members and the jaw adapter yoke. The proximal body portion of each jaw member can include a pivot aperture configured and adapted to receive the first pin. Each respective cam slot can be configured and adapted to receive the second pin. The second pin can be configured and adapted to translate within the cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration.

Each cam slot can include a proximal locking neck projecting into the cam slot defining a proximal locking area. The jaw members can be in the locked configuration when the second pin is proximal relative to the proximal locking neck in the proximal locking area. The proximal locking neck can include at least one of a protrusion projecting into the cam slot or a tapered portion. The jaw adapter yoke can include a proximal receiving portion and the proximal delivery catheter can include a spring release having a distal portion configured and adapted to be received within the proximal receiving portion of the jaw adapter yoke to transmit axial and rotational force to the jaw adapter yoke. A portion of the spring release between a terminal distal end of the spring release and the outwardly extending flange portion can have a constant diameter.

The proximal delivery catheter can include a drive wire coupled to a proximal portion of the spring release to transmit linear and rotational motion from the drive wire to the jaw adapter yoke. The proximal handle assembly can include an actuation portion coupled to a proximal end of the drive wire, and a grasping portion, wherein the actuation portion is configured and adapted to translate relative to the grasping portion to apply axial force to the drive wire. The proximal delivery catheter can include a spring tube, which is the same as the spring tube described above. The proximal delivery catheter can include a spring release, which is the same as the spring release described above.

In accordance with another aspect, a device for applying a hemostatic clip assembly includes a proximal delivery catheter including a proximal handle assembly and an elongated catheter body extending distally from the proximal handle assembly. The proximal delivery catheter includes a spring tube positioned at a distal end of the elongated catheter body, a drive wire movably positioned within the elongated catheter body, and a spring release coupled to a distal end of the drive wire, the elongated catheter body defining a longitudinal axis. The spring tube includes an inward projection and the spring release includes an outwardly extending flange portion configured and adapted to interact with the inward projection of the spring tube. A portion of the spring release between a terminal distal end of the spring release and the outwardly extending flange portion is a constant diameter. The device includes a distal clip assembly removably connected to a distal end of the elongated catheter body. The proximal delivery catheter is configured and adapted to transmit linear motion along the longitudinal axis and torsion about the longitudinal axis to at least a portion of the distal clip assembly.

The distal clip assembly can include a distal clip housing and a jaw assembly having a pair of cooperating jaw members fixed to the distal clip housing by a first pin. The first pin can be oriented orthogonally relative to the longitudinal axis, and a jaw adapter yoke can be operatively connected to the jaw members. At least one of the jaw members can be configured and adapted to rotate about the first pin and to rotate about the longitudinal axis. The distal clip housing can be the same as those described above. The distal clip assembly can include a second pin connecting between the jaw members and the jaw adapter yoke, similar to that described above. Each jaw member can include a proximal body portion wherein the proximal body portion of each jaw member can include a respective cam slot configured and adapted to receive the second pin and a pivot aperture configured and adapted to receive the first pin. The second pin can be configured and adapted to translate within the cam slots to move axially relative to the distal clip housing, as described above. Each cam slot can include a proximal locking neck projecting into the cam slot defining a proximal locking area, as described above. Each cam slot can define a distal portion and a proximal portion, wherein the distal portion of each cam slot is angled relative to the proximal portion of each cam slot. The jaw adapter yoke, spring release, distal clip housing, spring tube, and handle assembly can be the same as those described above.

In accordance with another aspect, a method for firing a hemostatic clip assembly includes positioning a distal clip assembly proximate to a target location and translating an actuation portion of a proximal handle assembly of a proximal delivery catheter relative to a grasping portion of the proximal handle assembly in at least one of a proximal direction or a distal direction. The distal clip assembly includes a distal clip housing, a jaw assembly having a pair of cooperating jaw members fixed to the distal clip housing by a first pin, and a jaw adapter yoke operatively connected to the jaw members. The proximal delivery catheter includes an elongated catheter body extending distally from the proximal handle assembly. The elongated catheter body defining a longitudinal axis. The actuation portion is operatively connected to the jaw adapter yoke via a drive wire and a spring release to transmit linear motion along the longitudinal axis and torsion about the longitudinal axis to the jaw adapter yoke. The linear motion of the jaw adapter yoke transmits the linear motion to a second pin positioned within a cam slot of at least one jaw member, thereby rotating at least one of the jaw members about the first pin and to rotate about the longitudinal axis. Each jaw member includes a rear opening connected to the cam slot and defining at least one proximal cantilever jaw arm. Translating the actuation portion includes translating the actuation portion in the proximal direction to transmit the linear motion in the proximal direction to the second pin to deflect the at least one jaw arm and lock the second pin behind a lock protrusion of the cam slot to lock at least one of the jaw members in a locked configuration.

Translating the actuation portion can include translating the actuation portion further in the proximal direction to transmit further linear motion in the proximal direction to the spring release, the further linear motion in a proximal direction de-coupling a distal portion of the spring release from a receiving portion of the jaw adapter yoke. Translating the actuation portion can include transmitting linear motion to the spring release in the proximal direction causing abutting between an inner diameter surface of at least one cantilever arm of a spring tube with an outwardly extending flange portion of the spring release. The spring tube can be coupled to a proximal end of the distal clip housing via the at least one cantilever arm. The abutting can cause the at least one cantilever arm to deflect radially outward and disengage from the proximal end of the distal clip housing.

In accordance with another aspect, a hemostatic clip assembly includes a distal clip housing defining a longitudinal axis, a jaw assembly having a pair of cooperating jaw members fixed to the distal clip housing by a first pin, and a jaw adapter yoke operatively connected to the jaw members. The jaw adapter yoke is configured and adapted to translate axially along the longitudinal axis and rotate about the longitudinal axis. At least one of the jaw members is configured and adapted to rotate about the first pin between an open configuration and a closed configuration. The first pin is oriented orthogonally relative to the longitudinal axis. Each jaw member includes a proximal body portion and a distal end effector. The proximal body portion of each jaw member includes a respective cam slot and a rear opening connected to the cam slot and defining at least one cantilever jaw arm.

The distal clip housing can include a pair of spaced apart arms, similar to those described above. The hemostatic clip assembly can include a second pin, similar to that described above. Each jaw member and its respective cam slot can be similar to those described above.

These and other features of a surgical device for applying a hemostatic clip assembly in accordance with the subject invention will become more readily apparent to those having ordinary skill in the art to which the subject invention appertains from the detailed description of the embodiments taken in conjunction with the following brief description of the drawings.

BRIEF DESCRIPTION OF THE DRAWINGS

So that those skilled in the art will readily understand how to make and use the gas circulation system of the subject invention without undue experimentation, embodiments thereof will be described in detail herein below with reference to the figures wherein:

FIG. 6 is a perspective view of a jaw adapter yoke of the device of FIG. 1 from a proximal direction, showing a proximal receiving portion of the jaw adapter yoke;

FIG. 7 is a cross-sectional perspective view of the jaw adapter yoke of FIG. 6, showing an inner surface of the proximal receiving portion;

DETAILED DESCRIPTION OF THE EMBODIMENTS

Figure 1:
FIG. 1 is a perspective view from the proximal direction of a device for applying a hemostatic clip assembly constructed in accordance with an embodiment of the present disclosure, showing a proximal delivery catheter having a proximal handle assembly and an elongated catheter body and the distal clip assembly.

Referring now to the drawings wherein like reference numerals identify similar structural elements and features of the subject invention, there is illustrated in FIG. 1 a surgical device for applying a hemostatic clip assembly in a patient, and more particularly, for separating the hemostatic clip assembly to function as a short-term implant constructed in accordance with an embodiment of the subject disclosure and is designated generally by reference numeral 10. Other embodiments of the generator control system in accordance with the disclosure are provided as will be described.

Figure 2:
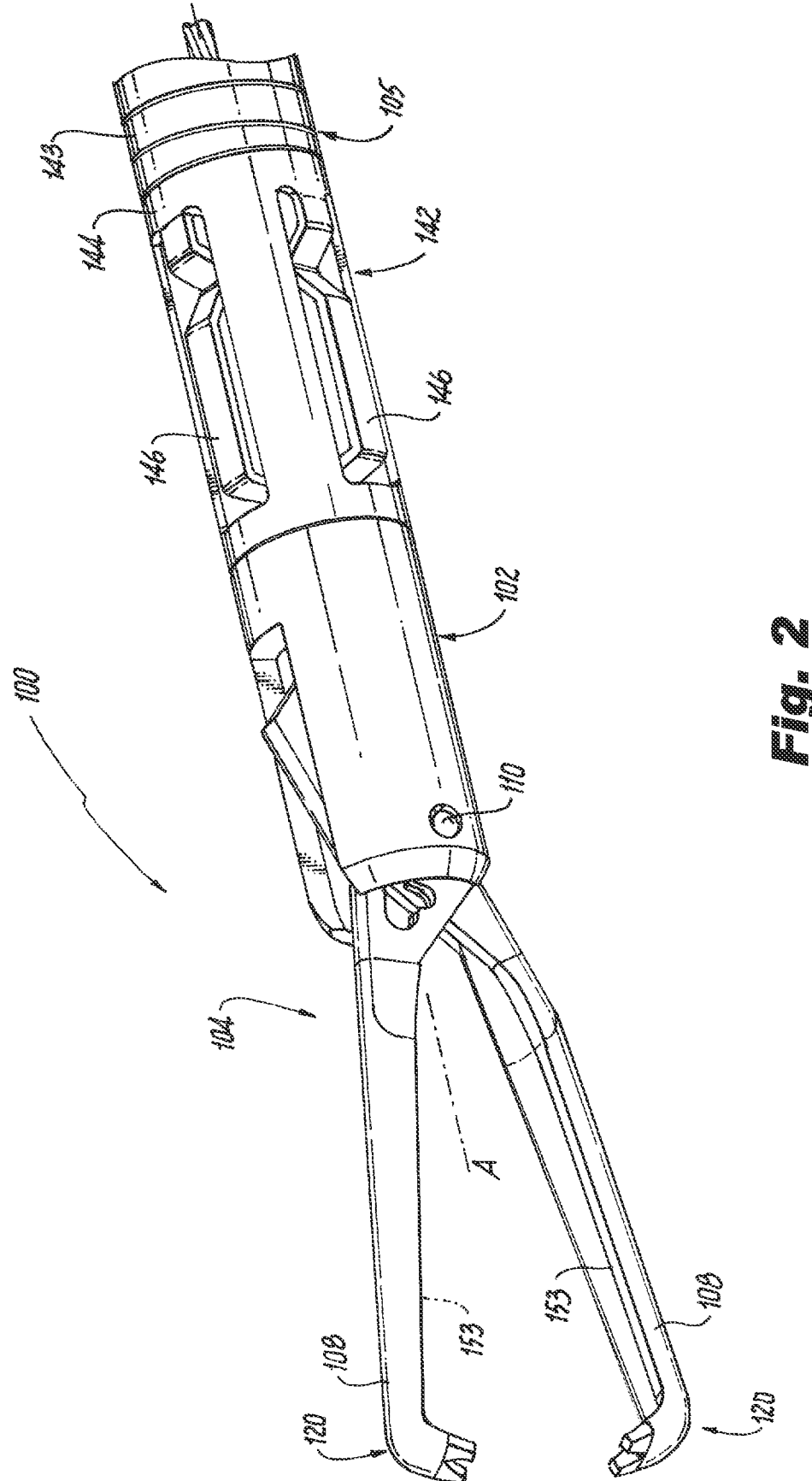
FIG. 2 is a perspective view of the distal clip assembly of FIG. 1, showing a jaw assembly with a pair of cooperating jaw members operatively connected to the distal clip housing.

As shown in FIGS. 1-2, a surgical device 10 for applying a hemostatic clip assembly 100 includes proximal delivery catheter 101 and the distal clip assembly 100. The distal clip assembly 100, e.g., a hemostasis clip, separates from the delivery catheter 101 to function as a short-term implant to stop and prevent re-bleeding, or in procedures such as ampullectomy, polypectomy, tissue repair and correction of other tissue defects. Such procedures are typically performed by grasping the tissue with the hemostatic clip. Using hemostatic clips in such procedures can result in benefits such as reduced trauma to the patient, low re-bleeding rate, reduced opportunity for infection, and decreased recovery time.

With continued reference to FIGS. 1-2, the proximal delivery catheter 101 has a proximal handle assembly 103 and an elongated catheter body 105 extending distally from the proximal handle assembly 103. The elongated catheter body 105 defines a longitudinal axis A. The proximal handle assembly 103 includes an actuation portion 115 coupled to a proximal end 111 of the drive wire 109, and a grasping portion 107. The actuation portion 115 is configured and adapted to translate relative to the grasping portion 107 to apply an axial force to the drive wire 109. Grasping portion 107 and actuation portion 115 are configured and adapted to rotate relative to a cap 170 and catheter body 105, thereby also rotating drive wire 109. Internal annular slots on the distal portion of grasping portion 107 interact with annular tabs on inside diameter of end cap 170 to prevent axial motion of actuation portion 115 and grasping portion but allow rotation.

Figure 3:
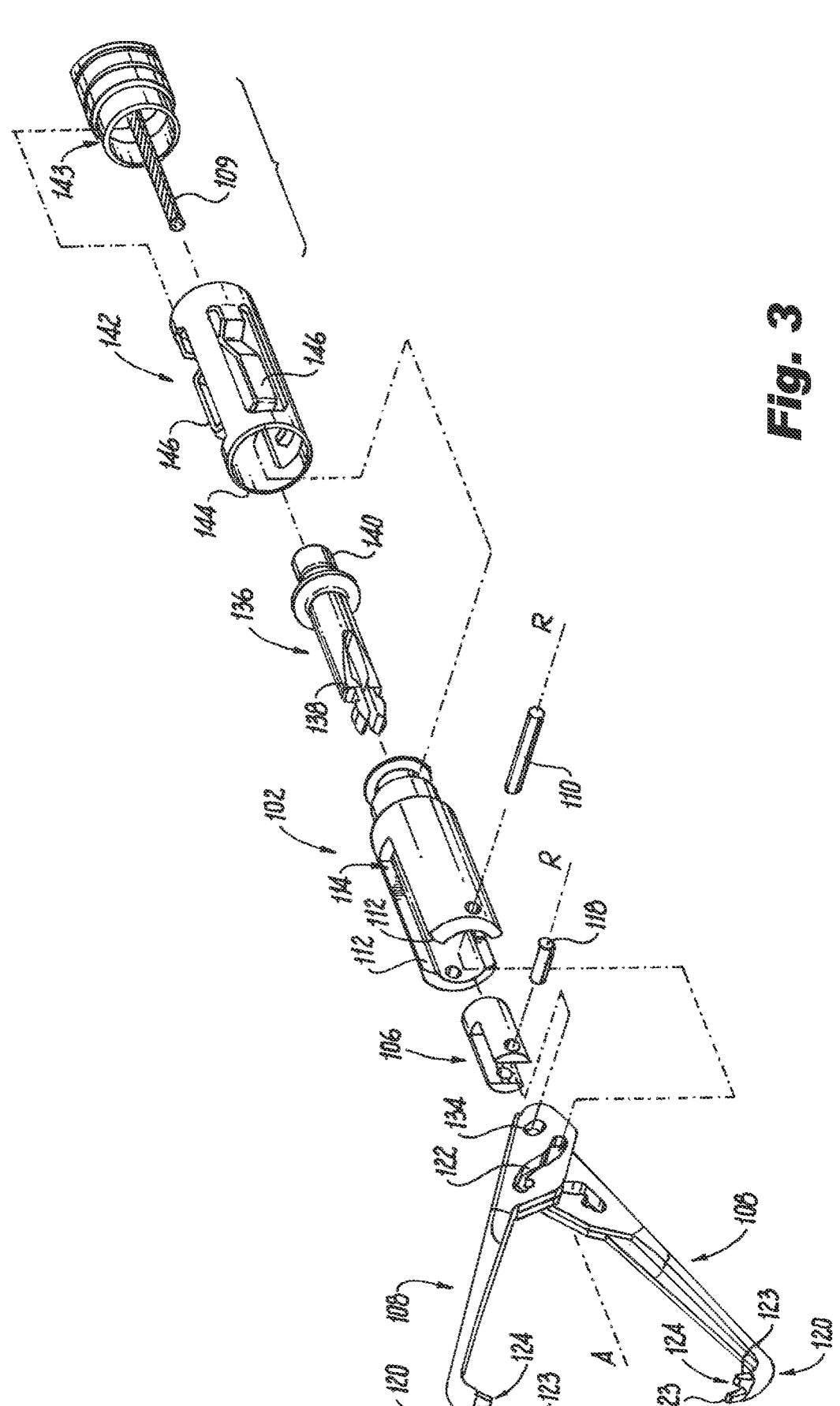
FIG. 3 is an exploded perspective view of a portion of the device of FIG. 1, showing the showing the distal end of the proximal delivery catheter and the distal clip assembly.

With continued reference to FIGS. 1-3, the proximal delivery catheter 101 includes a spring tube 142 between a proximal end of the distal clip assembly 100 and a distal end 143 of the catheter body 105. A proximal end 144 of the spring tube 142 mechanically coupled to the distal end 143 of the catheter body (e.g., at a coil portion) via weld, adhesive, or other means. The distal clip assembly 100 includes a distal clip housing 102 and a jaw assembly 104 slidably connected to the distal clip housing 102. The distal clip assembly 100 includes a jaw adapter yoke 106 positioned within the distal clip housing 102 and slidable relative to the distal clip housing 102. The jaw assembly 104 has a pair of cooperating jaw members 108 rotatably connected to the jaw adapter yoke 106 at a first pin 118 and slidably connected to the distal clip housing 102 by a second pin 110. The first and second pins 118 and 110, respectively, are oriented orthogonally relative to the longitudinal axis A. The first and second pins, 118 and 110, respectively, each define a respective pin rotation axis R. Both pin rotation axes R are orthogonal to the longitudinal axis A. The spring tube 142 includes cantilever arms 146 configured and adapted to be removably coupled to the distal clip housing 102, described in more detail below. The hemostatic clip assembly 100 is removably connected to a distal end 143 of the elongated catheter body 105 via the spring tube 142. The proximal delivery catheter 101 is configured and adapted to transmit linear motion along the longitudinal axis A and torsion about the longitudinal axis A to at least a portion of the distal clip assembly 100.

With reference now to FIGS. 2-3, the proximal delivery catheter 101 includes a spring release 136 having a distal portion 138 configured and adapted to be received within a proximal receiving portion 133 of the jaw adapter yoke 106. The jaw members 108 are configured and adapted to rotate about the first pin 118 between an open configuration and a closed configuration, and/or between a closed configuration and an open configuration, and to rotate about the longitudinal axis A. Jaw members 108 translate along longitudinal axis A and rotate about first pin 118 at the same time. Because first pin 118 is translating axially, the center of rotation is changing (the pin axis of first pin 118) as it shifts along the longitudinal axis A. Each jaw member 108 includes a proximal body portion 116 and a distal end effector 120. The proximal body portion 116 of each jaw member 108 includes a respective cam slot 122 configured and adapted to receive the second pin 110. Jaw members 108 are driven opened and/or closed by the second pin 110, e.g., a cam pin, as cam slots 122 of the jaw members 108 slide along second pin 110. The cam slots 122 are configured adapted to slide axially along second pin 110 relative to the distal clip housing 102 to move the jaw members 108 between the open configuration where respective distal tips 124 of the jaw members 108 are moved away from one another, the closed configuration where the respective distal tips 124 of the jaw members 108 are approximated towards one another to grasp tissue, and a locked configuration.

Figure 4:
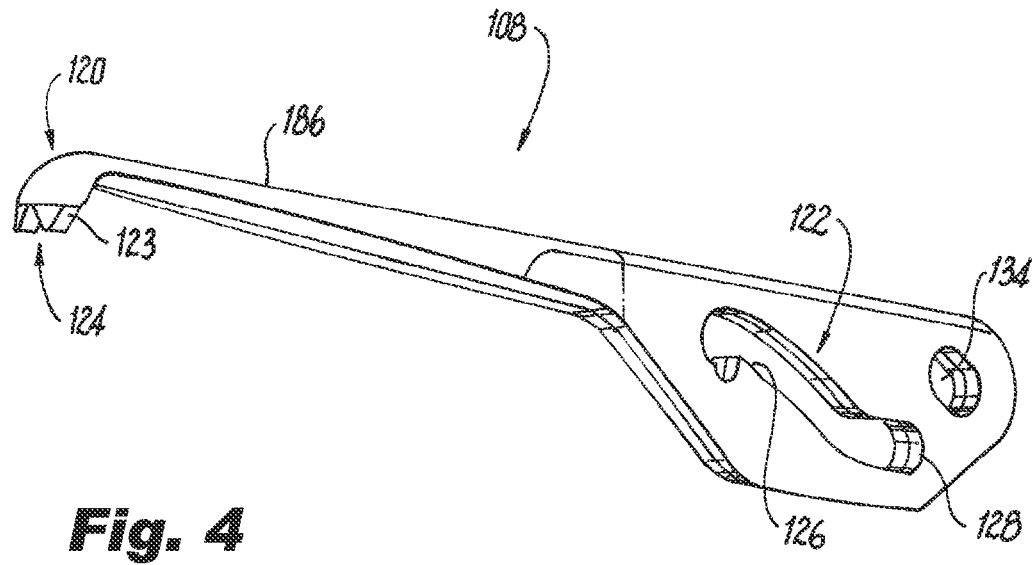
FIG. 4 is a perspective view of a jaw member of the device of FIG. 1, showing the cam slot.
Figure 5:
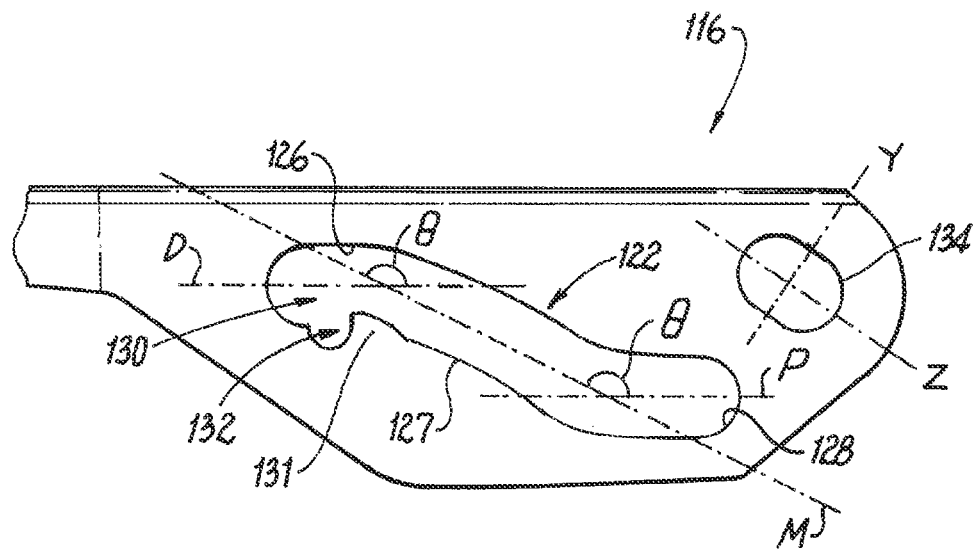
FIG. 5 is a side elevation view of a proximal portion of the jaw member of FIG. 4, showing proximal and distal portions of the cam slot.

With reference now to FIGS. 3-5, each jaw member 108 includes a pivot aperture 134 configured and adapted to receive the first pin 118. Pivot aperture 134 has an elongated shape, e.g., a pill shape, where the length of aperture 134 (along longitudinal aperture axis Z) is greater than a width of the aperture (defined along lateral aperture axis Y, orthogonal to axis Z). Pivot aperture 134 is configured and adapted to increase the included angle between jaw members 108 while in the open configuration, e.g. the angle shown between distal tips 120 of jaw members 108 in FIG. 14. Pivot aperture 134 is configured and adapted to also increase initial torque transferred to the clip arms 108 during the initiation of clip 100 closure. The distance between first pin 118 and second pin 110 as well as a comparison of a contact angle between cam slot 122 and second pin 110 with a contact angle between pivot aperture 134 and first pin 118 dictate the closing torque conversion at any given point in clip actuation. Generally, the contact angle for a given slot/aperture and its respective pin 118 or 110 can be defined as the angle between a tangent axis B and the longitudinal axis A, shown in FIG. 14. The tangent axis B is defined at the contact point between a surface of the given slot/aperture and a surface of its corresponding pin. The ratio between respective contact angles for pin 118 and pin 110 dictates the reaction forces of each pin/contact surface interaction such that, in some embodiments, the tangent axis B between pivot aperture 134 and first pin 118 can be configured so that initial motion of first pin 118 relative to the longitudinal aperture axis Z of pivot aperture 134 occurs earlier or simultaneous to relative displacement of second pin 110 within cam slot 122. This configuration increases the effective torque translated to jaw arms 108 for a given closing force. On the other hand, the embodiment of FIGS. 14-15, where initial motion of first pin 118 relative to the longitudinal aperture axis Z of pivot aperture 134 occurs after relative displacement of second pin 110 within cam slot 122, can offer a larger opening angle for jaw members 108 at maximum open position, while still providing substantially equivalent torque in the closed configuration.

With continued reference to FIGS. 3-5, the pivot aperture may extend at an angle relative to longitudinal axis A in order to further customize the force response curve. In particular, the longitudinal axis Z of pivot aperture 134 may create an angle between zero and forty-five degrees (0-45°) in either direction relative to the longitudinal axis A. Each jaw member 108 of the jaw assembly 104 is identical to the other member 108, allowing additional economy of scale. The distal end effectors 120 of each jaw member 108 include teeth 123 at their distal tips 124 that interlock with teeth of an abutting opposite jaw member. Teeth 123 positioned proximate to the side edge of their respective jaw member 108 optimize and maximize single-jaw tissue retention force during manipulation or tissue apposition, so as to catch tissue/defects easily, especially in non-perpendicular approaches to tissue. Jaw members 108 are stamped and then bent to have a 3D profile.

Figure 14:
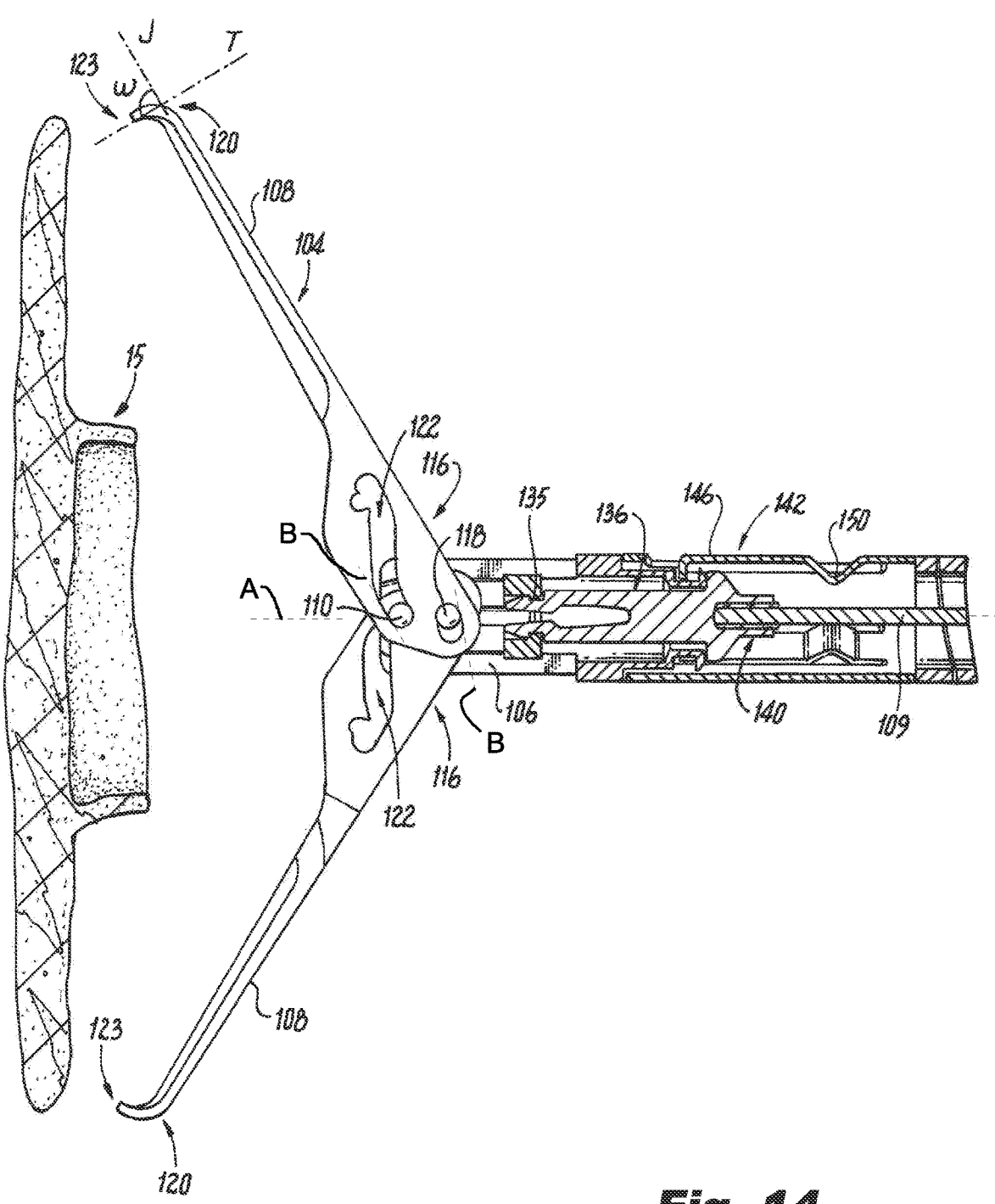
FIG. 14 is a cross-sectional side elevation view of a portion of the device of FIG. 1, showing the jaw members in the open configuration where respective distal tips of the jaw members are moved away from one another to grasp a target area of tissue.

As shown in FIGS. 2-5, the end effector 120 of each jaw member 108 includes an internal concave surface 153 which also helps to maximize tissue retention and capacity. A corresponding outer convex surface 186 aids in atraumatic and smooth insertion through an endoscope working channel. Those skilled in the art will readily appreciate that distal end effectors 120 can include at least one pointed tooth/peak, multiple peaks, of different or similar size at their distal tips 124. Distal end effectors 120 could also terminate in a combination of pointed peaks and rounded peaks to balance tissue pressure, allowing jaw members 108 to hook tissue with at least one peak and provide atraumatic contact with at least one peak. As shown in FIG. 14, the tooth (or teeth, peaks, etc.) may create an angle ω relative to an axis J of their respective jaw arms 108 between zero and 180 degrees, optimizing the approach angle of distal tips 124 relative to tissue surface. In the embodiment of FIG. 14, the angle ω of a tip axis T relative to axis J is approximately 90 degrees. It is contemplated, however, that the angle ω could be at 0 degrees, such that the tip simply extends from axis J, it could be at 45 degrees, or 180 degrees, where the tip is hooked around such that the tip axis T direction is parallel to axis J. The angle and design of jaw members 108 will be optimized for single jaw tissue retention force during manipulation or tissue apposition. The distance between the pivot aperture 134 and the cam slot 122 dictate the moment arm that translates axial translation to jaw rotation/actuation.

Figure 15:
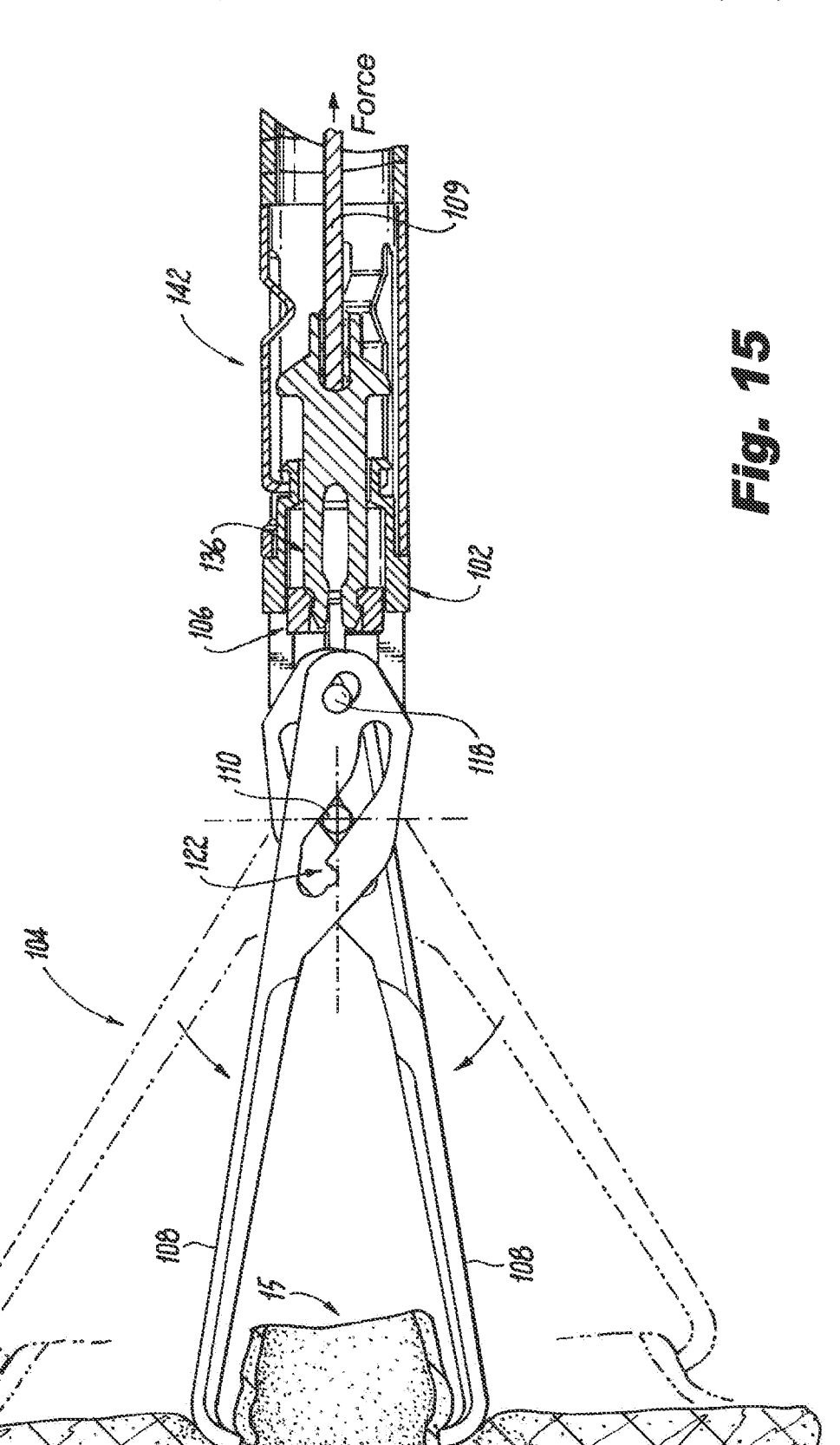
FIG. 15 is a cross-sectional side elevation view of a portion of the device of FIG. 1, showing the jaw members in a partially closed configuration where the respective distal tips of the jaw members are approximated towards one another to grasp tissue.
Figures 16, 17:
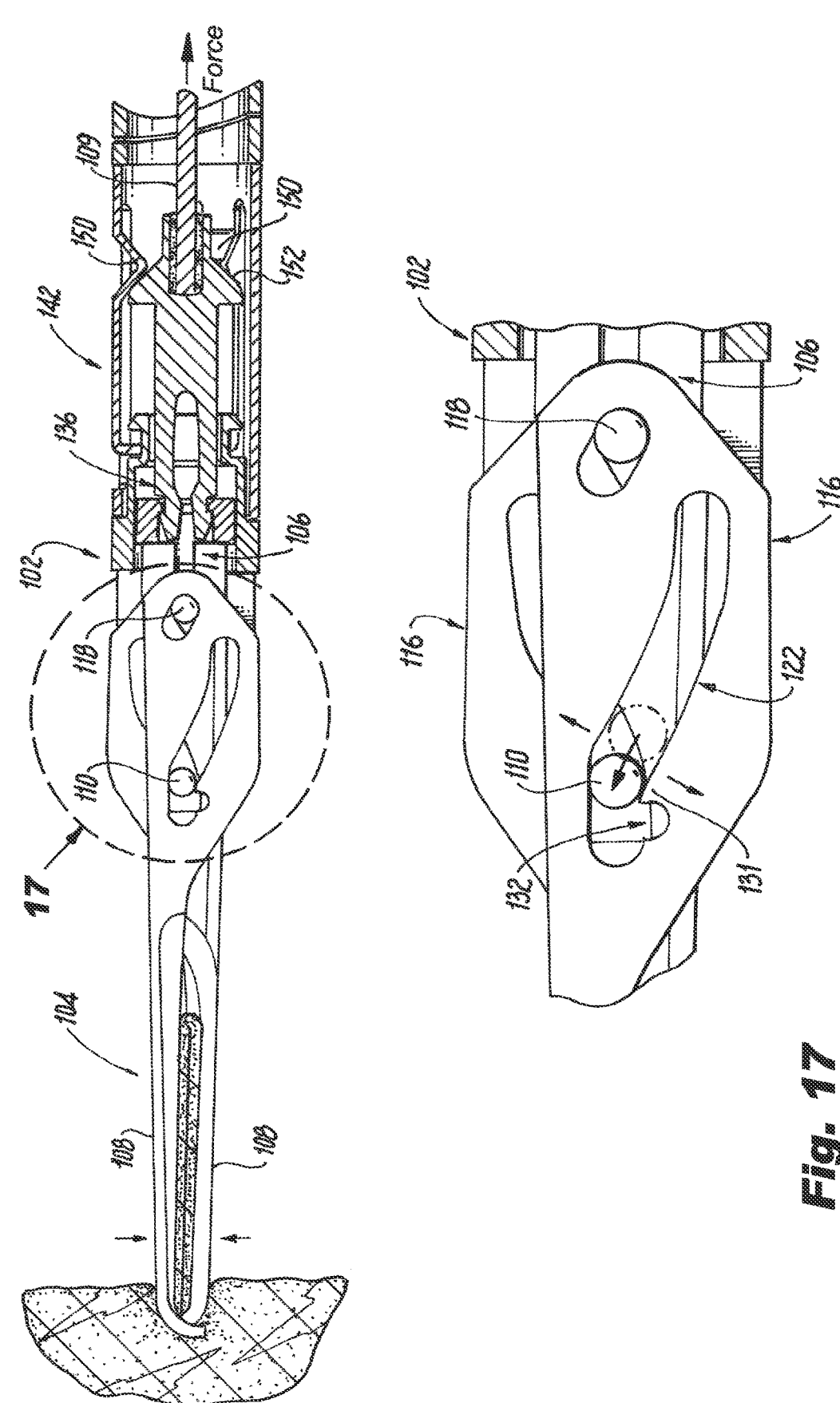
FIG. 16 is a cross-sectional side elevation view of a portion of the device of FIG. 1, showing the jaw members in a closed configuration where the respective distal tips of the jaw members are approximated towards one another to grasp tissue.
FIG. 17 is a cross-sectional side elevation detail view of a portion of the device of FIG. 1, schematically showing the transition of the second pin to a locked position within the cam slot.

As shown in FIGS. 4-5, each cam slot 122 defines a distal portion 126 and a proximal portion 128 with a middle portion 127 therebetween. The distal portion 126 and the proximal portion 128 of each cam slot 122 is angled relative to the middle portion 127 of each cam slot 122. The proximal portion 128 of each cam slot 122 defines a proximal axis P extending in a first direction. The distal portion 126 of each cam slot 122 defines a distal axis D. The middle portion defines a middle axis M extending in a second direction. The proximal axis P and the distal axis D are both at oblique angle θ relative to the middle axis M, as shown in FIGS. 14-16. The angle of a respective distal axis D or proximal axis P relative to middle axis M can be fine-tuned to provide optimal tissue clamping force given a user's maximum acceptable input force. While distal axis D and proximal axis P are shown substantially parallel to one another when in the closed configuration, thereby rendering the angle θ between axis P and axis M the same as the angle θ between axis D and axis M, those skilled in the art will readily appreciate that axes P and D may be oblique relative to one another.

With continued reference to FIGS. 4-5, each cam slot 122 includes a distal locking neck 130, e.g., a locking feature, projecting into the cam slot 122 defining a distal locking area 132. The jaw members 108 are in the locked configuration when the second pin 110 is distal relative to the distal locking neck 130 in the distal locking area 132. The distal locking neck 130 includes a protrusion 131 projecting into the cam slot 122. Lock protrusion 131, e.g., a detent, creates a narrowing of cam slot 122 to form the distal locking neck 130 that interferes with the outer diameter of the second pin 110 as it moves axially in the distal direction. The continued axial translation of pin 110 forces a widening of the cam slot 122 in an elastic manner and creates an additional resistance force on the internal drivetrain, e.g., spring release 136 and spring tube 142. Once the second pin 110 crests the inflection point on the protrusion 131, it will snap into place distally in front of the protrusion 131, effectively locking the jaws in a closed position. The shape of lock protrusion can vary and can be an arcuate, triangular, or slanted feature. Lock protrusion 131 may also be achieved by reversing the slope of cam slot 122 such that it inflects passed the 0-degree orientation with respect to the axis A of the catheter, described in more detail below. Various embodiments for the distal locking neck are described below in FIGS. 27-29.

As shown in FIGS. 3 and 6-7, the jaw adapter yoke 106 includes pin apertures 160 and is operatively connected to the jaw members 108 via first pin 118. Jaw members 108 are configured to rotate about first pin 118. The jaw adapter yoke 106 is circular component with two arms 113 extending towards the distal end of the yoke 106 that form a slot 161 therebetween. The slot 161 allows the proximal portions 116 of the jaw members 108 rotate around first pin 118. One of the apertures 160 is formed in each arm 113 and is in a transverse direction to a longitudinal axis of the jaw adapter yoke 106 and the longitudinal axis A of the catheter body 105. The apertures 160 receive the first pin 118 and can be assembled using orbital riveting or laser tack welding. The jaw adapter yoke 106 includes a proximal receiving portion 133 and slides linearly inside of distal clip housing 102 to drive jaw members 108 and their respective cam slots 122 axially along the second pin 110. The proximal receiving portion 133 of the jaw adapter yoke 106 includes an inner axially facing surface 135 that mates with a snap feature 141 (described below) at axially facing mating surface 156 the distal portion 138 of spring release 136, allowing linear force transmission up to a predetermined value. Friction due to an interference fit between an inside surface 129 of yoke 106 and an outside surface 159 of spring release 136 (shown in FIGS. 10-11) allows torque transmission from drive wire 109 to the distal subassembly. In some embodiments, the proximal receiving portion 133, e.g., the circular hole, could have an inner surface with a rectangular cross section where flats 155 of spring release 136 could transmit torque between spring release 136 jaw adapter yoke 106 via the rectangular inner surface of proximal receiving portion 133.

Figure 8:
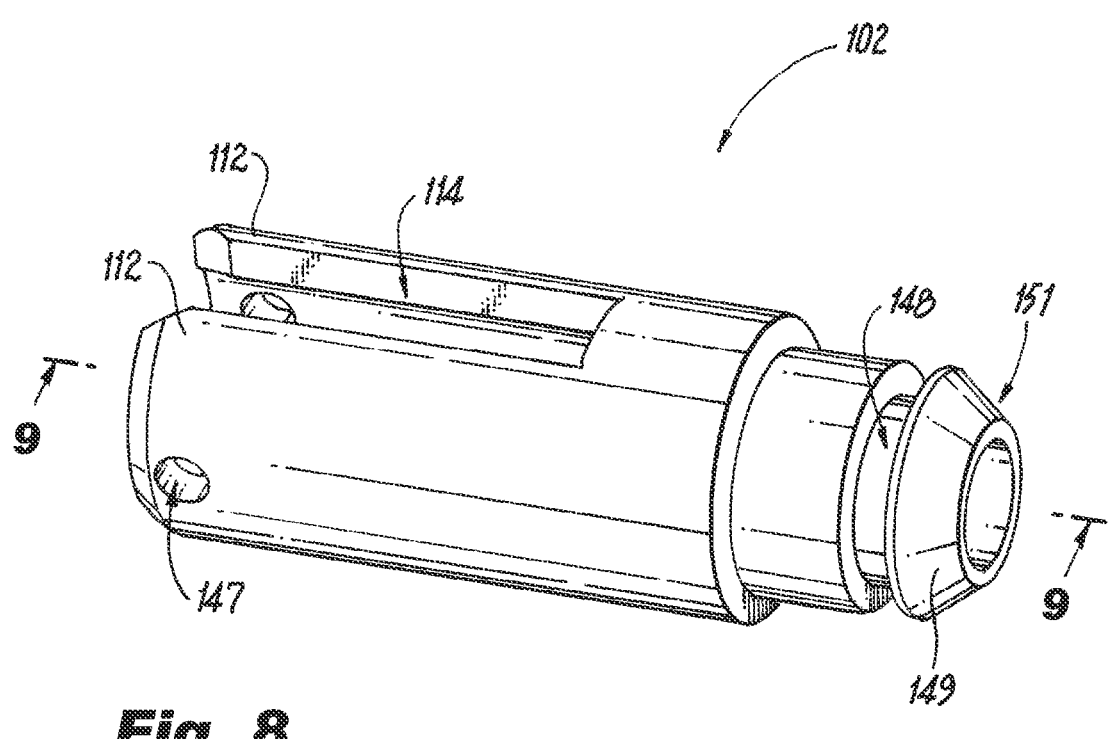
FIG. 8 is a perspective view of a distal clip housing of the device of FIG. 1 from a proximal direction, showing the circumferential slot defined about the periphery of a proximal end of the distal clip housing.
Figure 9:
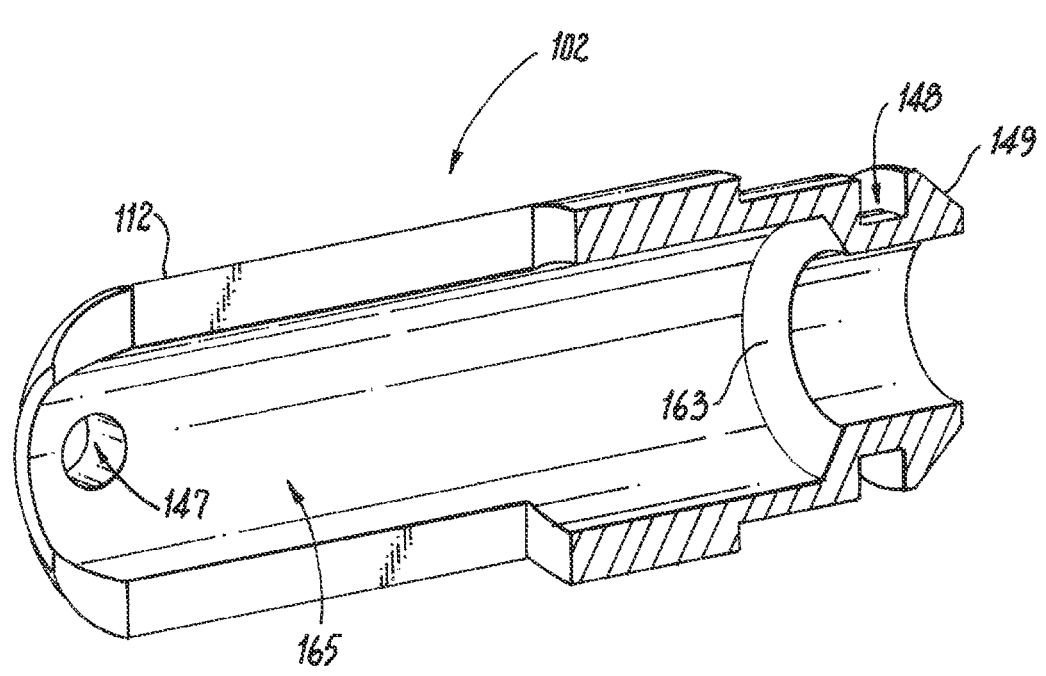
FIG. 9 is a cross-sectional perspective view of the distal clip housing of FIG. 8; showing a distal facing stop surface.

As shown in FIGS. 3 and 8-9, the distal clip housing 102 includes a pair of spaced apart arms 112 defining a slot 114 configured and adapted to provide clearance for respective proximal portions 116 of the jaw members 108 to rotate relative the first pin 118. The distal clip housing 102 connects via a snap fit connection to the spring tube 142 via a circumferential slot 148, e.g., a stepped retention ring, defined about a periphery of a proximal end 151 of the distal clip housing 102. The distal clip housing 102 includes a tapered outer diameter portion 149 proximal relative to the circumferential slot 148. During assembly of the distal clip assembly 100 to the proximal delivery catheter 101, the tapered outer diameter portion 149 pushes the cantilever arms 146 of the spring tube 142 radially outward allowing the 90 degree bent tabs (e.g., the inwardly extending flanges 158 described in more detail below) to seat in the circumferential slot 148 of distal clip housing 102. An inner surface 165 of distal clip housing 102 further includes a distal facing stop surface 163. The inner diameter surface 165 of distal clip housing 102 allows for axial transmission of jaw adapter yoke 106, until jaw adapter yoke 106 contacts the hard stop created by distal facing stop surface 163.

With reference to FIGS. 3, 10-11 and 14, the distal portion 138 of the spring release 136 is configured and adapted to transmit axial and rotational force to the jaw adapter yoke 106. The distal portion of the spring release 136 is divided into at least two tines 139 with a slot 117 therebetween. The tines 139 form a snap feature 141 at the distal most tip of each tine 139. The snap feature 141 includes a tapered outer diameter surface 145 at the distal tip of each tine 139 and an annular mating surface 156 selectively engageable with an inner surface 135 of the receiving portion 133 of the jaw adapter yoke 106. Annular mating surface 156 allows linear force transmission up to a predetermined value. Different deployment forces can be easily achieved by varying dimensions spring release 136. Varying the diameter of annular mating surface 156 will have great effect on the release force, as will changing the length C of tines 139 (which thereby adjusts the length of the slot 117 between tines 139). The slot 117 must be long enough so as to not cause plastic deformation during the assembly process. Slot 117 may also be non-axisymmetric so as to stiffen one tine 139 relative to the other. This could bias the release mechanism so that one tine 139 always deflects first, increasing repeatability in force design. Those skilled in the art will also readily appreciate that receiving portion 133 could also have an inner surface with a square cross-section such that flat outer surfaces 155 on tines 139 interface with inner diameter surface to transmit torque.

With continued reference to FIGS. 3, 10-11 and 14, the drive wire 109 is mechanically coupled to a proximal portion 140 of the spring release 136 to transmit linear and rotational motion from the drive wire 109 to the jaw adapter yoke 106. The proximal portion 140 of the spring release 136 being the portion proximal relative to tines 139. The spring release 136 includes a receiving bore 162 opening in the proximal direction for receiving and coupling the drive wire 109 to the spring release 136. The rotation of drive wire 109 about the longitudinal axis A drives rotation of spring release 136, jaw adapter yoke 106, distal clip housing 102 and jaw assembly 104 about the longitudinal axis A relative to catheter body 105 and spring tube 142. The spring release 136 includes an outwardly extending flange portion 152. Between the outwardly extending flange portion 152 and proximal terminal end 119 of the spring release 136 is a continuous constant diameter portion 154 having a diameter D. The invention will present a novel deployment mechanism for a hemostatic clip. The novel design allows for a shorter deployed clip body and proposes an improved disconnecting feature.

Figures 38, 39:
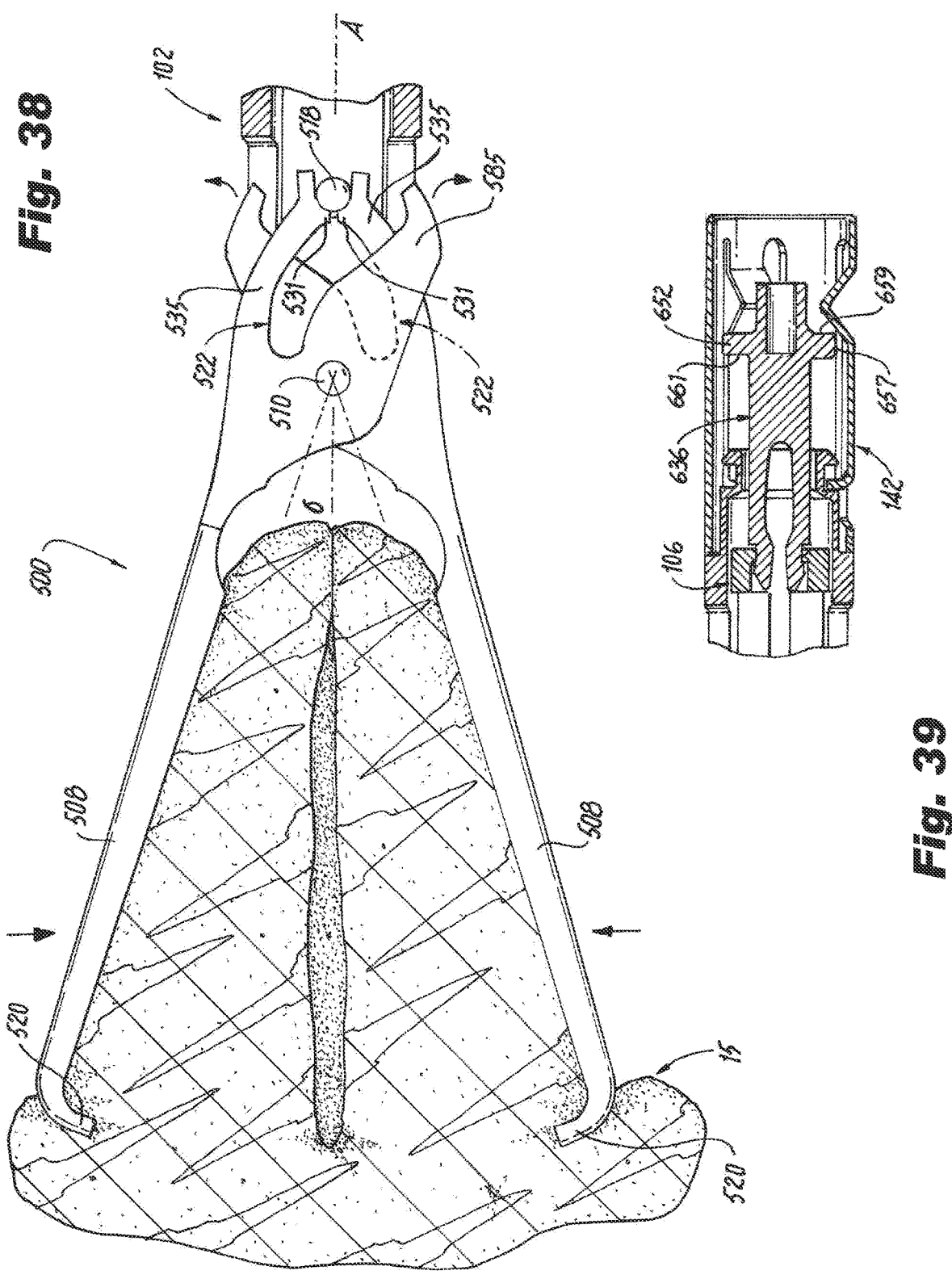
FIG. 38 is a cross-sectional side elevation detail view of a portion of the device of FIG. 30, showing the jaw members in a locked configuration before firing with a 20-degree angle in the locked position.
FIG. 39 is a cross-sectional side elevation detail view of a portion of the device of FIG. 1, showing an alternative embodiment for a spring release where the outwardly extending flange portion does not include a taper.

As shown in FIG. 39, those skilled in the art will readily appreciate that spring release 636 can be used in conjunction with device 10 in lieu of spring release 136. Spring release 636 is the same as 136 except that the outwardly extending flange 652 of spring release 636 has an outer surface 657 with a circular cylinder shape. In other words, both a proximal facing surface 659 of flange 652 and a distal facing surface 661 of 652 are orthogonal relative to the longitudinal axis A.

As shown in FIGS. 2-3 and 12-13, the cantilever arms 146 of the spring tube 142 can be laser cut or stamped from the tube body, creating at least one cantilever arm 146. Each cantilever arm 146 includes an inwardly extending flange 158 that removably engages with a circumferential slot 148 defined about a periphery of a proximal end 151 of the distal clip housing 102. The inwardly extending flange 158 is a 90-degree tab bent inwards that mates with corresponding circumferential slot 148 of jaw housing. The spring release 136 is positioned at least partially within the spring tube 142. The spring tube 142 includes inwardly extending v-shaped projection 150, e.g., a first formed feature. Spring tube 142 is welded or mechanically coupled to the coil at the distal end 143 of the catheter body 105 which secures spring tube 142 to proximal delivery catheter 101.

Figure 18:
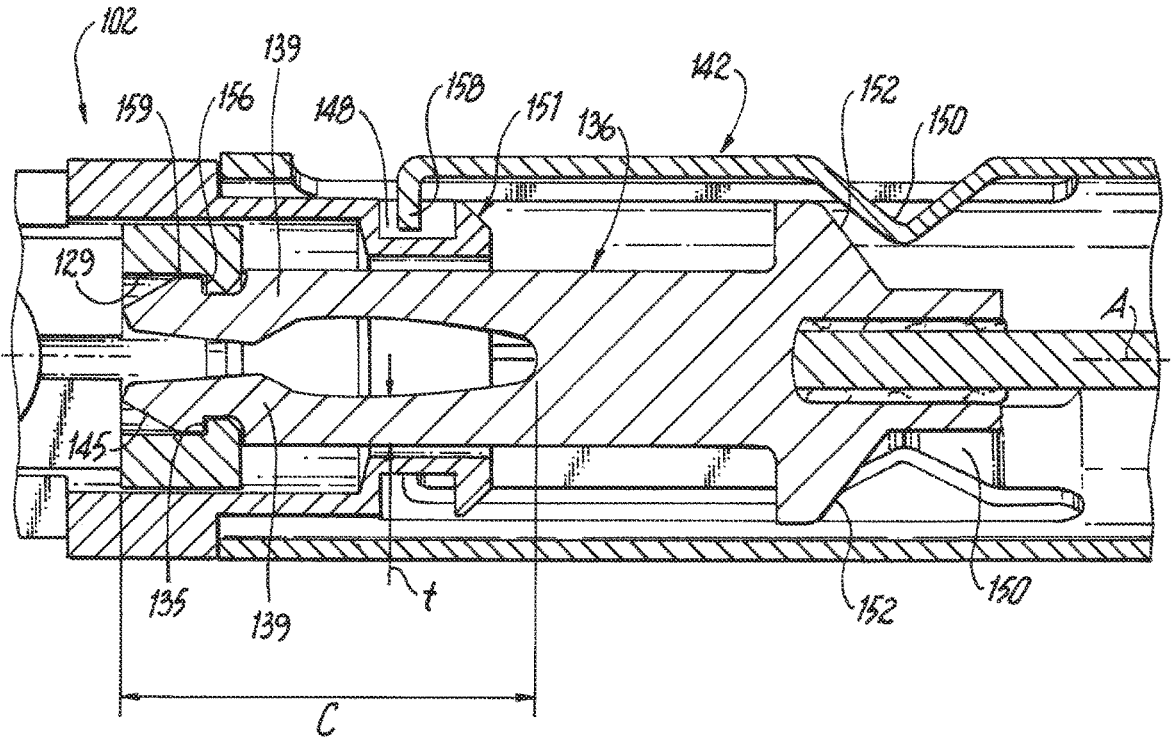
FIG. 18 is a cross-sectional side elevation view of a portion of the device of FIG. 1, showing the spring release engaged with the jaw adapter yoke in the closed configuration.

With reference now to FIGS. 14-17, some of the various configurations of device 10 are shown. In FIG. 14, the device 10 is in an open configuration and the jaw members 108 and their respective cam slots 122 are translated in a distal most position relative to second pin 110. In FIG. 15, the device 10 is shown between the open and the closed configuration and the first pin 118, yoke 106 and spring release 136 are translated in a more proximal position relative to the distal clip housing and relative to the open configuration of FIG. 14. Additionally, in FIG. 15 as compared to FIG. 14, cam slots 122 slid proximally along with their jaw members 108 relative to second pin 110, such that second pin 110 is in a more distal portion of the cam slots 122. In FIG. 15, second pin 110 is still proximal of the locking neck 130 and the protrusion 131. In FIG. 16, the closed configuration is shown. In FIGS. 16-17, the respective distal tips 124 of the jaw members 108 are approximated towards one another to grasp tissue 15 (but not necessarily in abutment with one another). In FIGS. 16-18, the device 10 is closed, but not locked, meaning that second pin 110 is still proximal of the protrusion 131.

Figure 19:
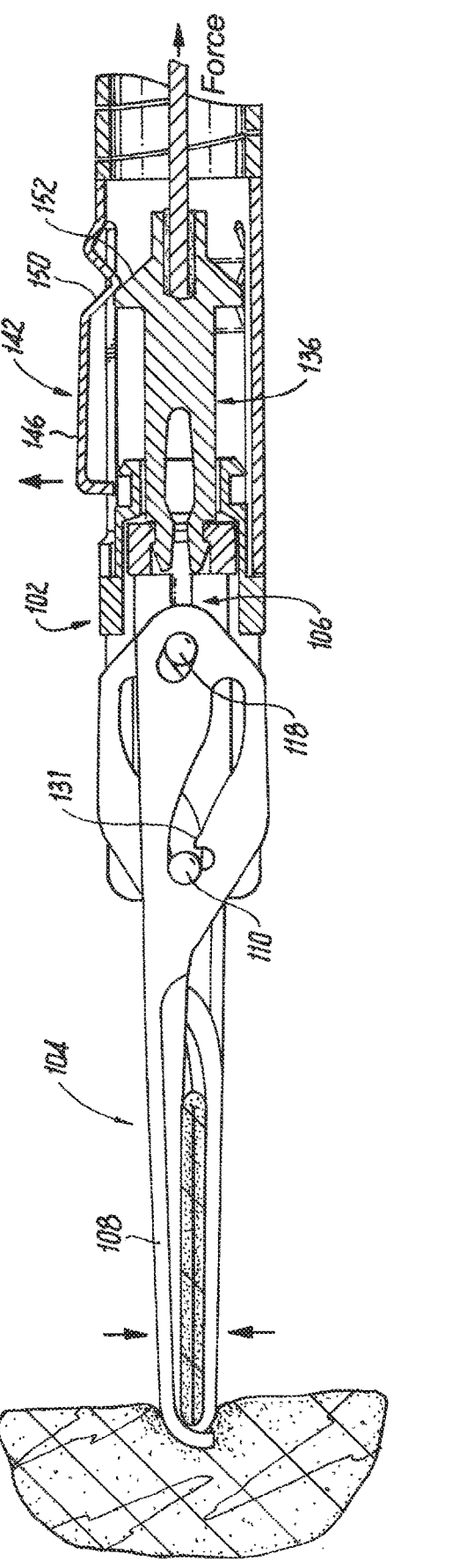
FIG. 19 is a cross-sectional side elevation detail view of a portion of the device of FIG. 1, showing the jaw members in a locked configuration before firing.

In FIGS. 16-19, the device 10 transitions from a closed configuration (FIGS. 16-18) to a locked configuration (FIG. 19). From the closed configuration, the continued axial translation in the distal direction of second pin 110 forces a widening of cam slot 122 in an elastic manner (as indicated schematically by the arrows in FIG. 17) and creates an additional resistance force on the internal drivetrain. Once second pin 110 crests the inflection point on the protrusion 131, it will snap into place behind the protrusion 131, effectively locking the jaw members 108 in a closed position, shown in FIG. 19. Because the drive wire 109 only transmits limited compression, a user will generally not be able to translate sufficient force from the handle distally to second pin 110 relative to the protrusion 131 to unlock the second pin 110 from the locking area 132. In the locking configuration, the second pin 110 is in a distal position relative to the locking necks 130 and their respective protrusions 131. In the locked configuration, the second pin 110 is within the distal locking area 132 of each cam slot 122.

Figures 20, 21, 22:
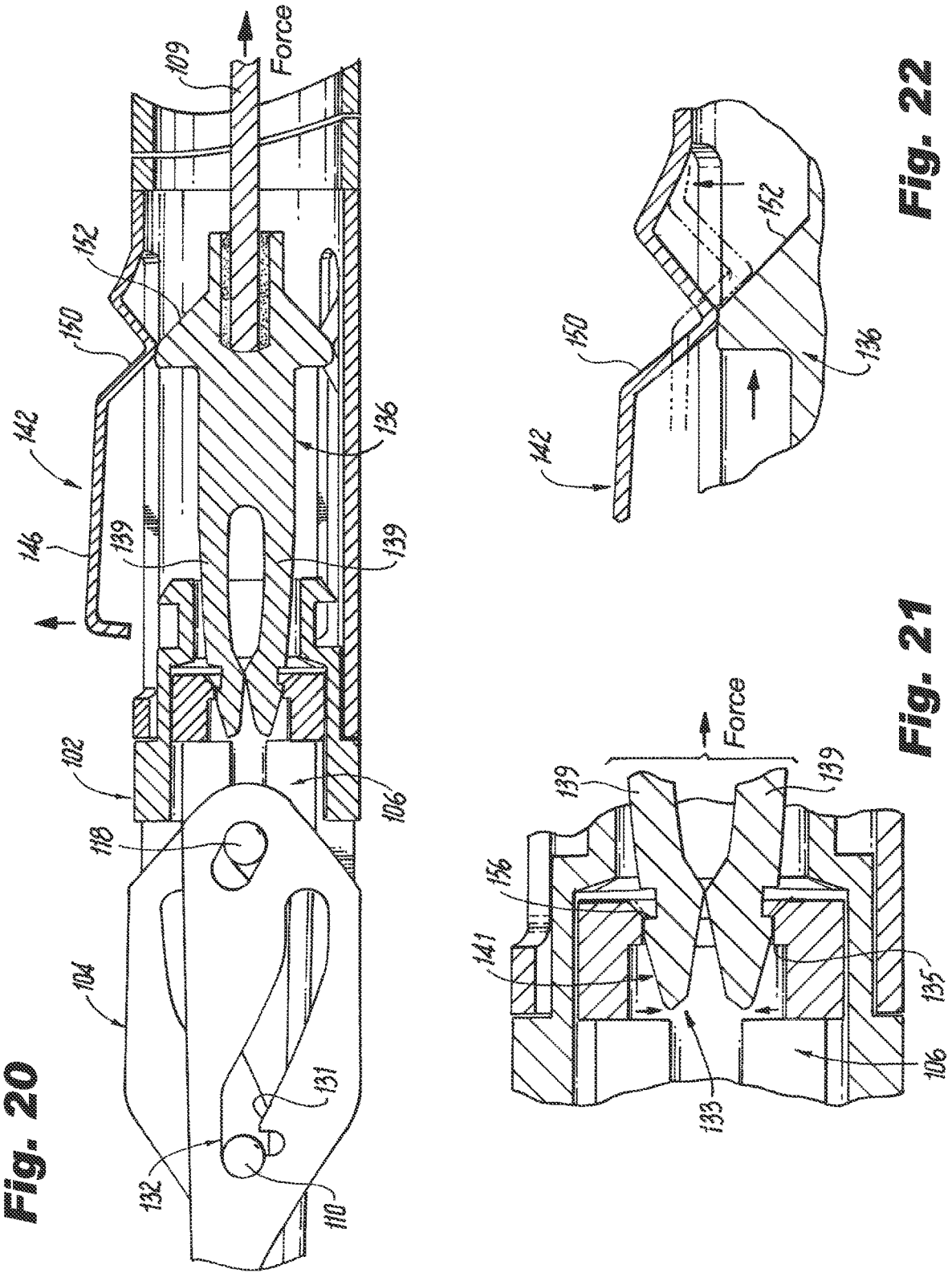
FIG. 20 is a cross-sectional side elevation detail view of a portion of the device of FIG. 1, showing the release of the spring release from the jaw adapter yoke and the release of the spring tube from the distal clip housing when firing the device.
FIG. 21 is a cross-sectional side elevation detail view of a portion of the device of FIG. 1, schematically showing the inward deflection of the tines of the spring release as they move proximally relative to the jaw adapter yoke when firing the device.
FIG. 22 is a cross-sectional side elevation detail view of a portion of the device of FIG. 1, schematically showing the outward deflection of the cantilever arm of the spring tube as the spring release moves proximally relative to the spring tube when firing the device.

As shown in FIGS. 20-22, once the second pin 110 is in the distal locking area 132, further axial movement of the spring release 136 in a proximal direction (e.g., away from the tissue 15) acts to "fire" the distal clip assembly 100 by releasing the distal clip assembly 100 from the proximal delivery catheter 101. The further linear motion of the spring release 136 in the proximal direction puts the spring release 136 in tension against jaw adapter yoke 106 due to abutment between mating surface 156 of the snap feature 141 and the inner surface 135 of the receiving portion 133. This tension causes each tine 139 to act as a spring and deflect inwardly, shown schematically by the inwardly pointing arrows in FIG. 21, and release from the receiving portion 133. The release force required to detach spring release 136 from the adapter yoke 106 can be tuned by adjusting the length C of each tine 139, the thickness t of each tine 139, and/or the angle of mating surface 156 relative to the longitudinal axis A, shown in FIG. 18. The angle of mating surface 156 relative to longitudinal axis A is shown as 90 degrees, but can range from 30 to 90 degrees, e.g., 45 degrees. The ratio of length C to thickness t can range from 8:1 to 10:1, e.g., 9:1. These dimensions provide the desired elastic behavior to ensure consistent release.

With continued reference to FIGS. 20-22, as the spring release 136 moves proximally relative to the jaw adapter yoke 106, it also moves proximally relative to the spring tube 142, thereby causing abutment between an inner diameter surface of the v-shaped flange portions 150 of the cantilever arms 146 of a spring tube 142 with an outwardly extending flange portion 152 of the spring release 136. The abutting causes each cantilever arm 146 to deflect radially outward and disengage the inwardly extending flanges 158 from the circumferential slot 148 at the proximal end 151 of the distal clip housing 102. Full disengagement (e.g., "firing") of the distal clip assembly 100 is realized through both the inward deflection of the tines 139 of spring release 136 and the outward deflection of the cantilever arms 146 of spring tube 142.

Figures 23, 24, 25:
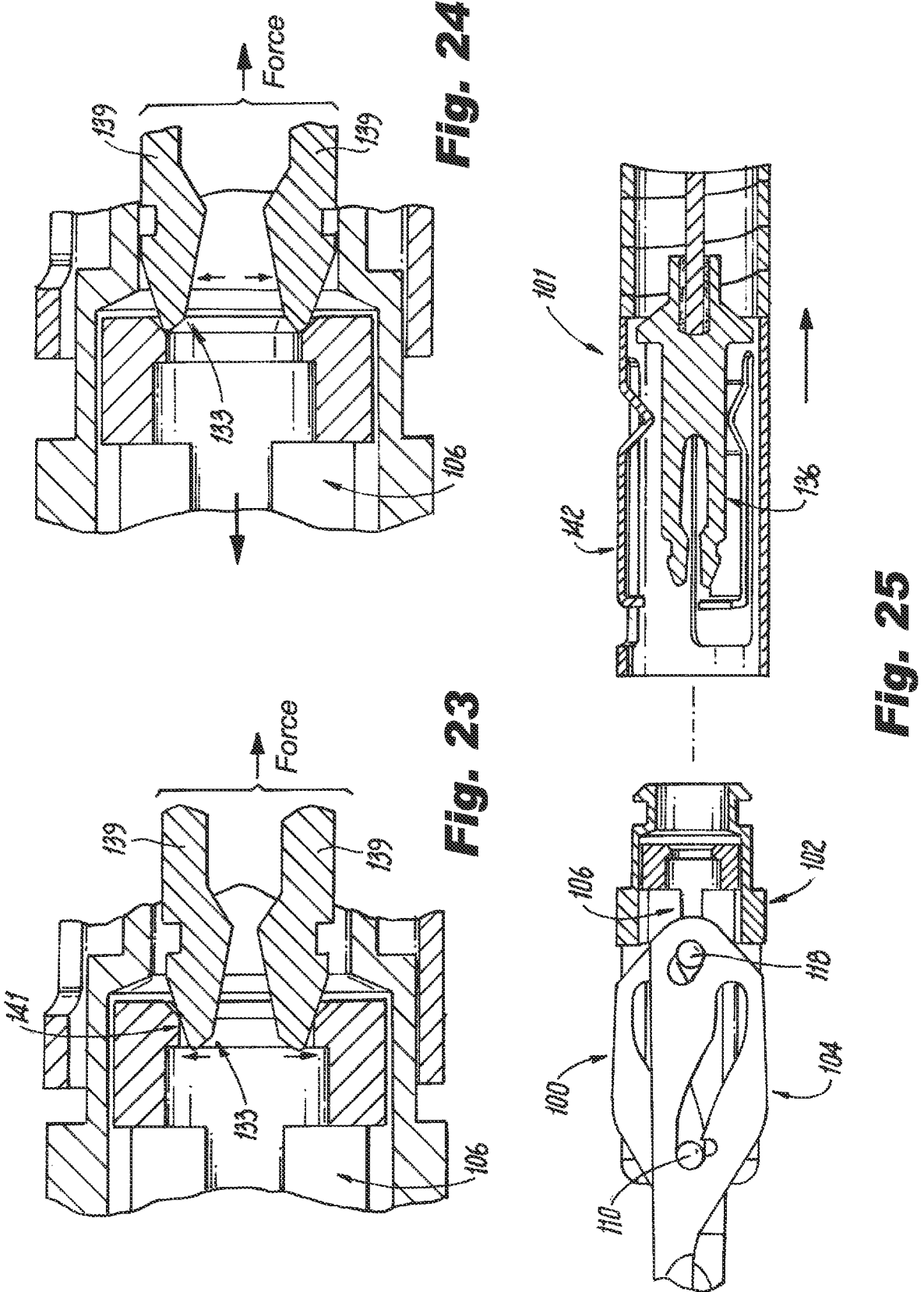
FIG. 23 is a cross-sectional side elevation view of a portion of the device of FIG. 1, showing the spring release disconnecting from the jaw adapter yoke for removal of the proximal delivery catheter.
FIG. 24 is a cross-sectional side elevation view of a portion of the device of FIG. 1, showing the spring release disconnected from the jaw adapter yoke for removal of the proximal delivery catheter.
FIG. 25 is a perspective view of a portion of a device for applying a hemostatic clip is a cross-sectional side elevation view of a portion of the device of FIG. 1, showing the proximal delivery catheter separated from the distal clip assembly.

As shown in FIGS. 20-25, a single spring component, spring release 136, disengages two springs (tines 139 and cantilever arms 146) generating an improved disconnect mechanism that enhances the ability to reposition the clip assembly 100 prior to deployment by simplifying the feedback to the user into a single tactile signal, decreasing the likelihood of user confusion as to whether or not the clip 100 has fully deployed. In the embodiment of FIGS. 20-25, cantilever arms 146 arms begin deflecting first, but the final displacement of extending flange portion 152 relative to cantilever arms 146 occurs simultaneously with the deflection of internal spring release 136. In addition to the simplified user feedback, it also makes accidental deployment of the clip assembly 100 less likely, as fewer components are used to realize disengagement. Because there are fewer components, less space is needed in the distal clip assembly 100, allowing for a shorter clip body. The shorter clip "stem" or overall length of deployed clip relative to jaw size is seen as an improvement. Additionally, the firing mechanism is elastic, and permanent deformation, e.g., breakage, is not required to deploy the clip assembly 100. As such, deployment can be reversible in some embodiments to a certain extent, which allows for the possibility of a multi-use delivery catheter. As shown in FIG. 25, after firing, proximal delivery catheter 101 can then be removed from the surgical site, leaving the distal clip assembly 100 to function as a short-term implant.

Furthermore, after firing, spring release 136 can continue to move proximally and recede into catheter body 105. Because of the continuous constant diameter portion 154 between the outwardly extending flange portion 152 and proximal terminal end 119 of the spring release 136, the after-firing user feedback after the firing is a sudden reduction in force required on actuator 115. Contrary to some designs seen in the prior art, where there may be a stop flange on a spring release to prevent spring release from receding further, present embodiments provide the user a definitive tactile feedback by way of a sudden reduction in force (from the firing) and allows the handle to displace far past its normal operation longitudinal stroke without resistance, reducing the chance that a user will mistake the retraction of spring release 136 with firing. Both of these factors aid the user in determining successful deployment of distal clip assembly 100.

A method for firing a hemostatic clip assembly, e.g., distal clip assembly 100, includes positioning the distal clip assembly proximate to a target location, e.g., near tissue as shown in FIG. 14, and translating an actuation portion, e.g., actuation portion 115, of a proximal handle assembly, e.g., proximal handle assembly 103, of a proximal delivery catheter, e.g., proximal delivery catheter 101, relative to a grasping portion, e.g., grasping portion 107, of the proximal handle assembly in at least one of a proximal direction or a distal direction. The actuation portion is operatively connected to a jaw adapter yoke, e.g., jaw adapter yoke 106, via a drive wire, e.g., drive wire 109, and a spring release, e.g., spring release 136 to transmit linear motion to the jaw adapter yoke. The linear motion of the jaw adapter yoke transmits a linear component of motion to at least one jaw member, e.g., jaw member 108, and its cam slot, e.g., cam slot 122, to translate the cam slot along a second pin, e.g., second pin 110, connecting between at least one of the jaw members and the distal clip housing, thereby rotating at least one of the jaw members about the first pin between an open configuration and a closed configuration, and/or between the closed configuration and the open configuration.

The method includes translating the actuation portion in the proximal direction to transmit the linear motion in the proximal direction to the cam slot, as shown in FIG. 15, to lock the second pin behind a lock protrusion, e.g., lock protrusion 131, of the cam slot to lock at least one of the jaw members in a locked configuration, as shown in FIG. 16. Translating the actuation portion includes translating the actuation portion in the proximal direction to transmit linear motion in the proximal direction to the spring release, as shown in FIG. 18. The linear motion in a proximal direction de-coupling a distal portion, e.g., distal portion 138, of the spring release from a receiving portion, e.g., receiving portion 133, of the jaw adapter yoke, as shown in FIGS. 20-25.

Figure 26:
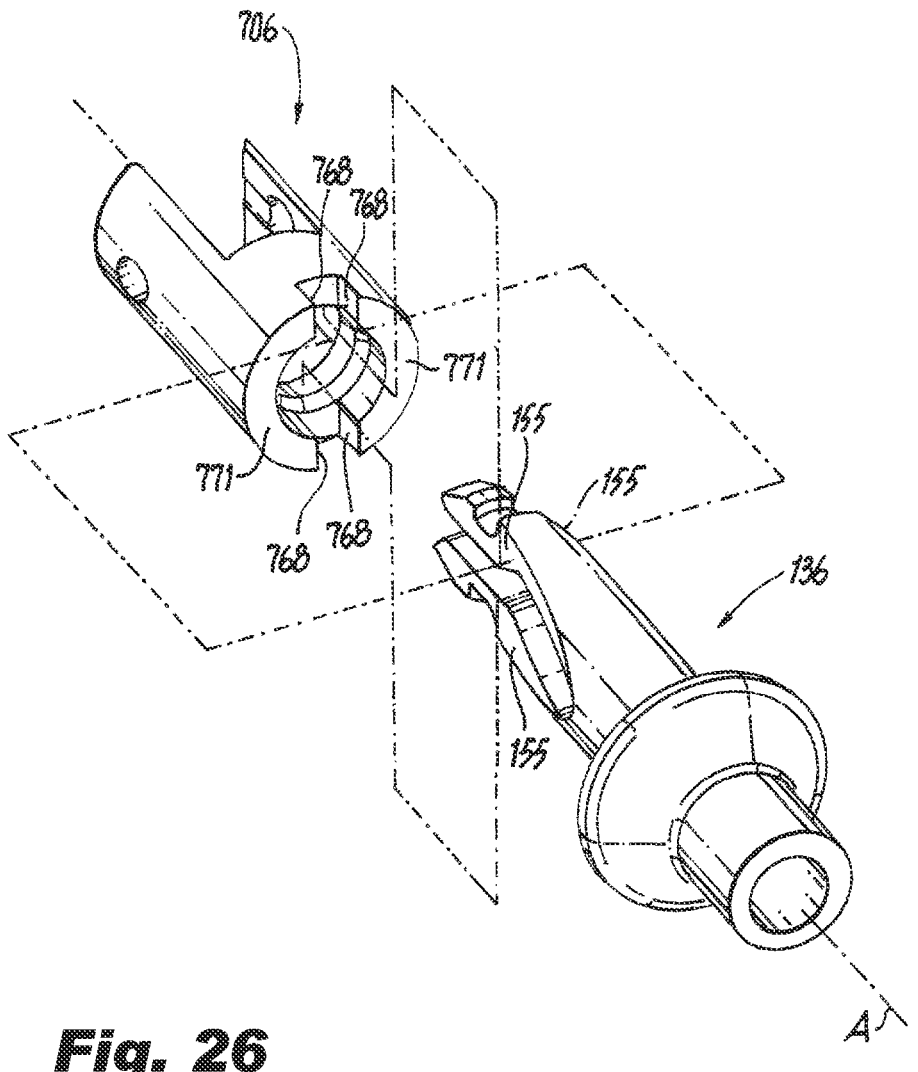
FIG. 26 is a perspective view of portions of another embodiment of a release pin and another embodiment of a jaw adapter yoke constructed in accordance with the present disclosure, showing the jaw adapter yoke having flat bosses extending from a proximal end to engage with flat outer surfaces on tines of the spring release.

As shown in FIG. 26, another embodiment for torque transmission in device 10 is shown. In FIG. 26, spring release 136 is the same as that described above. A jaw adapter yoke 706 is generally the same as jaw adapter yoke 106, except that yoke 706 includes rectangular bosses 771. Jaw adapter yoke 706 can be used in device 10 in lieu of jaw adapter yoke 106. In FIG. 26, the flat portions 155 of tines 139 abut bosses 771 having flat surfaces 768 extending from the proximal end of the jaw adapter yoke 706 that interface with the aforementioned flat portions 155 of tines 139 such that rotation of the spring release 136 about longitudinal axis A transmits torque to jaw adapter yoke 706, thereby also transmitting torque to the jaw members 108 and housing 102.

Figure 27:
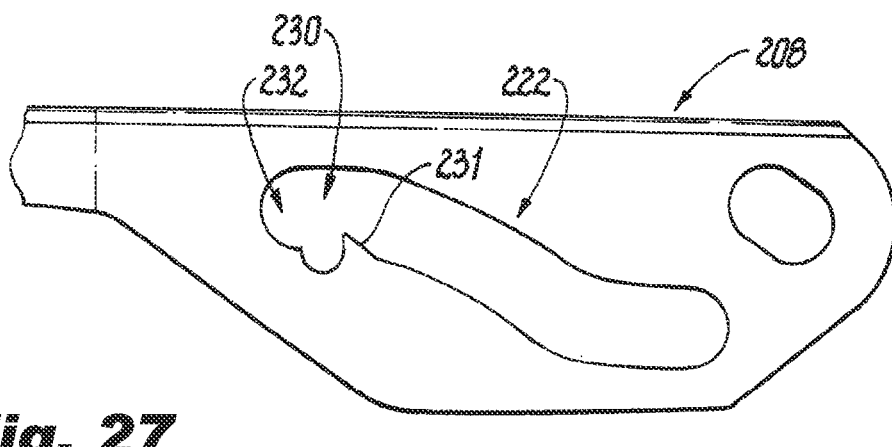
FIG. 27 is a side elevation view of another embodiment of a jaw member for use with the device for applying a hemostatic clip assembly of FIG. 1, showing a tapered portion.
Figure 28:
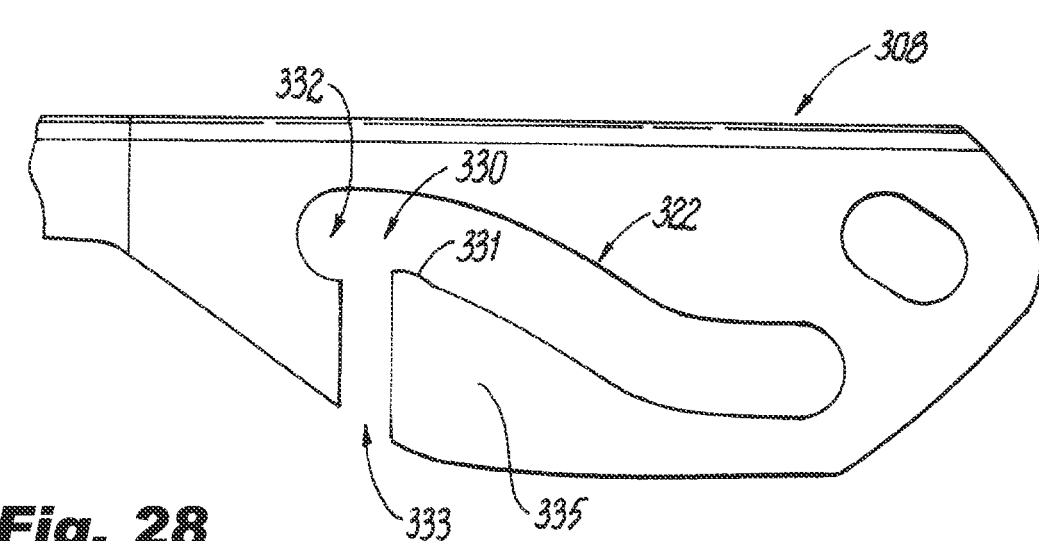
FIG. 28 is a side elevation view of another embodiment of a jaw member for use with the device for applying a hemostatic clip assembly of FIG. 1, showing a slot in the jaw member.
Figure 29:
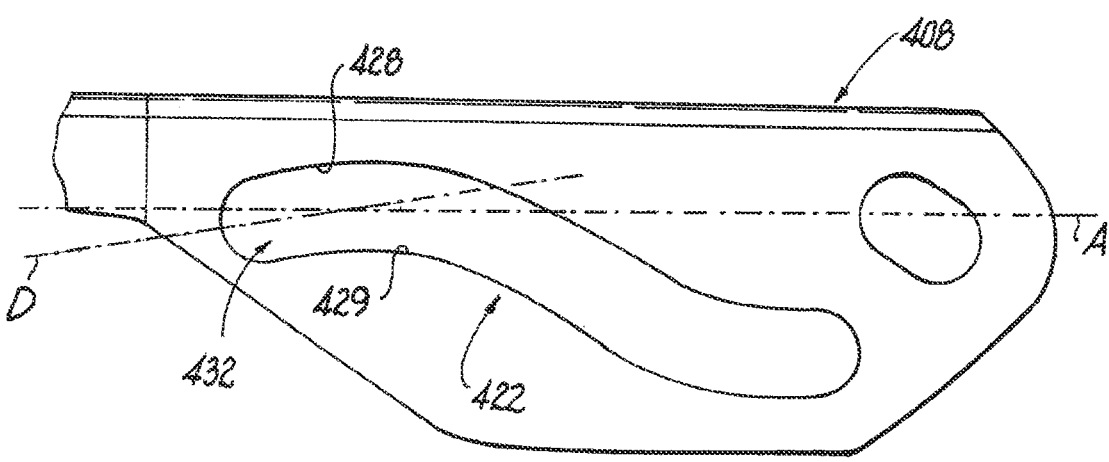
FIG. 29 is a side elevation view of another embodiment of a jaw member for use with the device for applying a hemostatic clip assembly of FIG. 1, showing a reverse slope in the distal portion of the cam slot.

Referring now to FIGS. 27-29, several different embodiments for the jaw members are described. In FIG. 27, an embodiment of a jaw member 208 is shown. Jaw member 208 is similar to jaw members 108 in that it can be used in the jaw assembly 104 and the distal clip assembly 100. Jaw member 208 also includes a distal end effector 220 similar to distal end effector 120. The main difference between jaw member 208 and jaw member 108 is that jaw member 208 includes a cam slot 222 in a proximal portion 216 of the jaw member 208 where the cam slot 222 includes a locking neck 230 formed by a tapered portion 231, e.g., a linear triangular ramp, where protrusion 131 is more of an arcuate ramp. Once the cam pin (e.g., pin 110) crests the inflection point on the ramp 231, it will snap into place distally in front of the ramp 231, effectively locking the jaw members 208 in a closed position. This geometry allows an easier transmission of axial force to normal force on the internal walls of cam slot 222, requiring less force to initiate locking. The proximal end of triangle locking ramp 231 will also prevent axial transmission of the cam pin after locking is achieved.

As shown in FIG. 28, another embodiment of a jaw member 308 is shown. Jaw member 308 is similar to jaw members 108 in that it can be used in the jaw assembly 104 and the distal clip assembly 100. Jaw member 308 also includes a distal end effector similar to distal end effector 120. The main difference between jaw member 308 and jaw member 108 is that jaw member 308 includes a cam slot 322 in a proximal portion 316 of the jaw member 308 having a locking neck 330 formed by a protrusion 331. A distal locking area 332, similar to locking area 132, is defined by the locking neck 330. Additionally, the protrusion 331 terminates in a slot 333. Slot is oriented orthogonally to a longitudinal axis of the jaw member 108, which when in the closed configuration, is generally parallel to the longitudinal axis A. This open slot 333 creates a cantilever lock arm 335 on the bottom wall of cam slot 322. This results in a decreased force required to lock the clip, and results in a higher rate of successful locking in instances where the jaw members 308 are not perfectly parallel to each other, as deflection in the cantilever lock arm 335 can accommodate some axis offset of the jaw members 308. A distal locking area 332, similar to locking area 132, is positioned distally from the protrusion 331.

As shown in FIG. 29, another embodiment of a jaw member 408 is shown. Jaw member 408 is similar to jaw member 108 in that it can be used in the jaw assembly 104 and the distal clip assembly 100. Jaw member 408 also includes a distal end effector similar to distal end effector 120. The main difference between jaw member 408 and jaw member 108 is that jaw member 408 includes a cam slot 422 in a proximal portion 516 of the jaw member 408 having a locking neck 430 formed by a slope reversal on a distal portion 428 of the cam slot 422. In other words, instead of a distal axis D of distal portion 428 being parallel to a longitudinal axis A of a catheter body, e.g., catheter body 105, distal axis D is angled radially outward relative to axis A resulting in a locking force due to cantilever deflection. In this instance, the user will feel a gradual increase in feedback force, and then a sudden decrease. Once a cam pin, e.g., second pin 110, has crested an inflection point 429 of the pin track (again, relative to the longitudinal axis of the clip body, which is parallel to longitudinal axis A of catheter body at rest) the slope direction changes and begins to force the clip open ever so slightly (0-10 degrees of angulation between jaws. Subsequent unlocking of the jaw members 408 would require equal proximal movement of the cam pin relative to a pivot pin, e.g., second pin 110, which is prevented by the spring force required to pass the cam pin over the inflection point during distal translation. Again, an elongate drive wire, e.g., drive wire 109, will not be able to transmit sufficient compressive force to actuate the cam pin distally, effectively locking the clip. The cam slot 422 of jaw member 508 has the as the added benefit of accommodating some amount of tissue thickness between the jaw members 408 without incurring bending stress in the jaw members 408.

Figure 10:
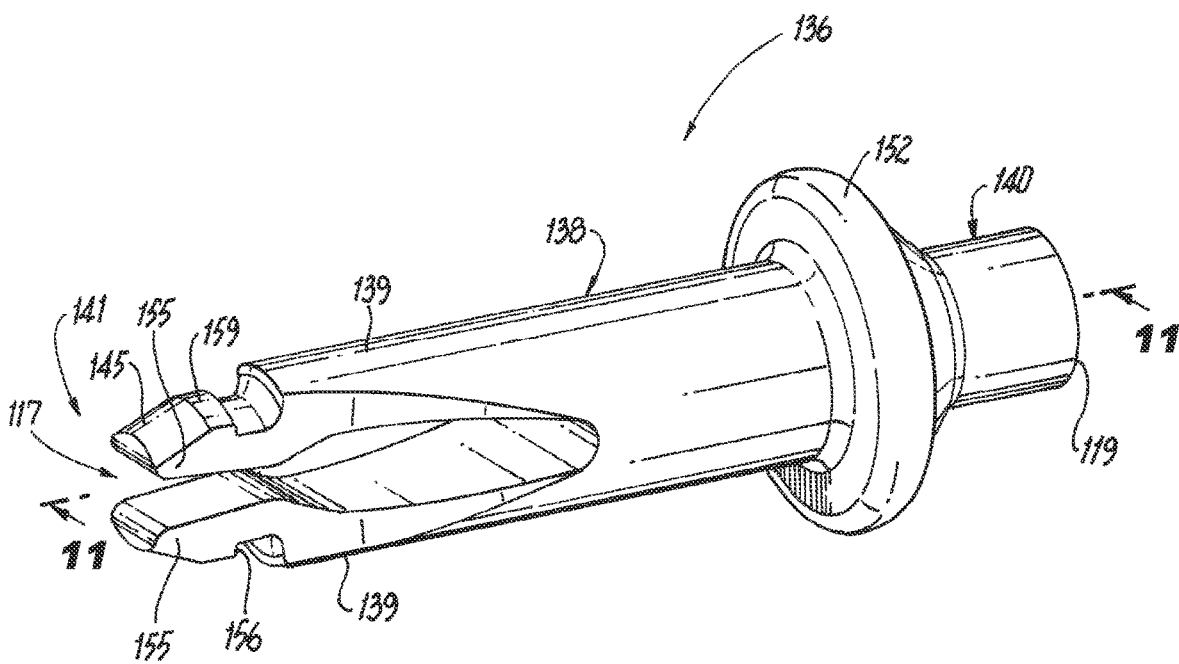
FIG. 10 is a perspective view of a spring release of the device of FIG. 1 from a distal direction, showing a distal portion of the spring release.
Figure 11:
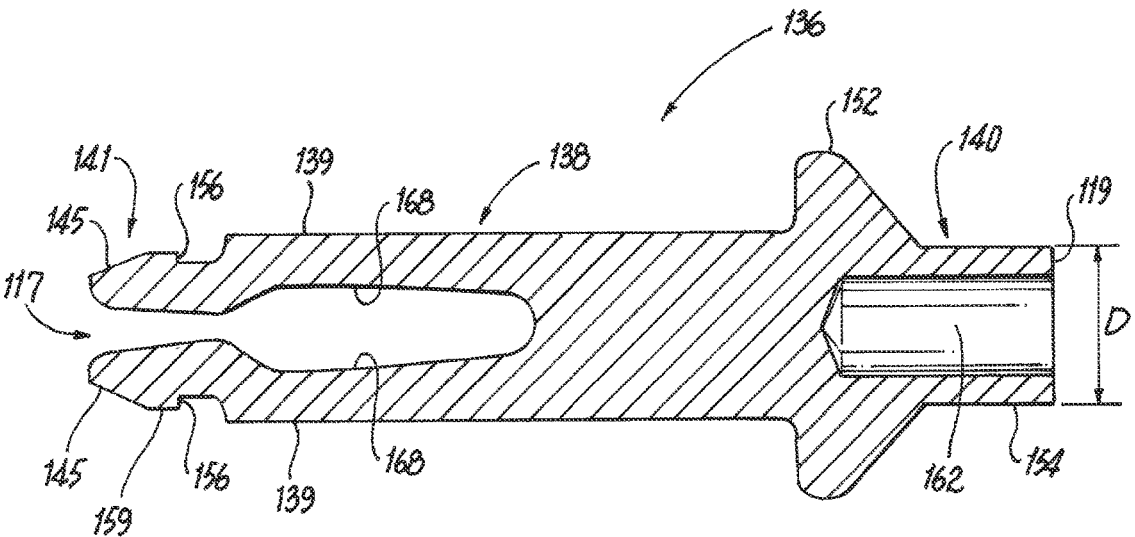
FIG. 11 is a cross-sectional side elevation view of the spring release of FIG. 10; showing the mating surfaces of the tines of the distal portion of the spring release.
Figure 12:
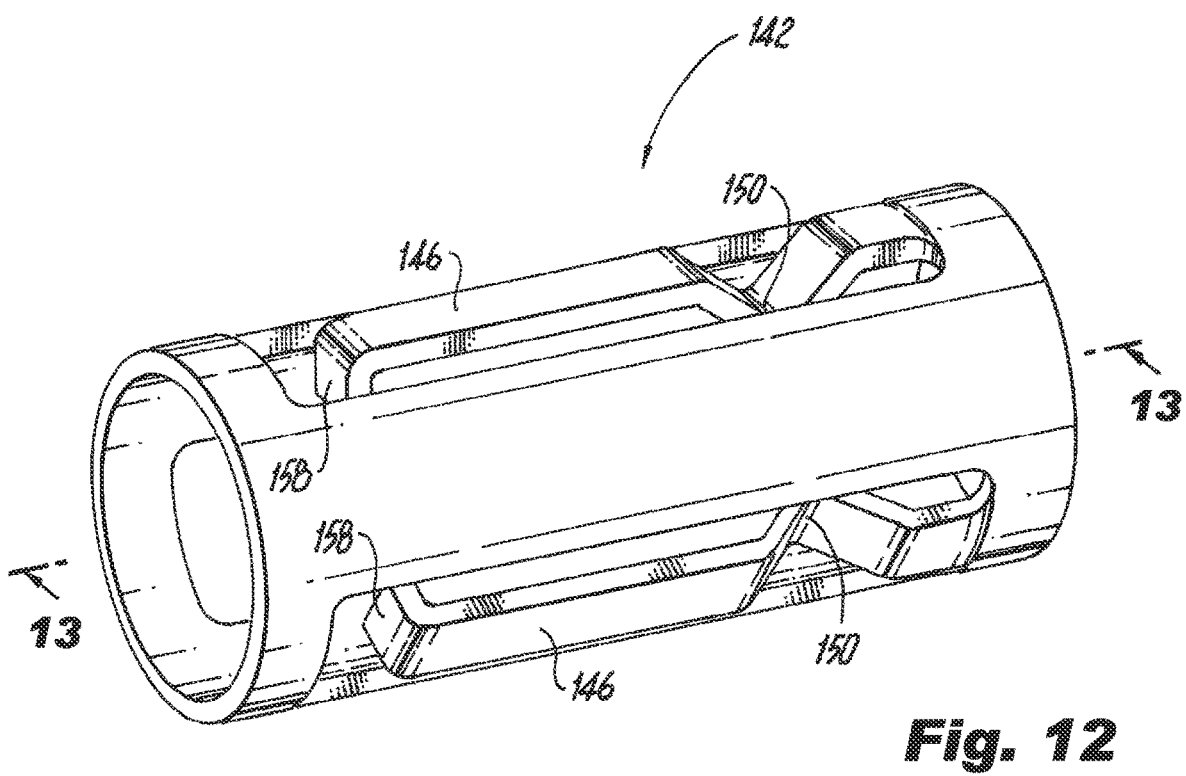
FIG. 12 is a perspective view of a spring tube of the device of FIG. 1 from a distal direction, showing cantilever arms of the spring tube.
Figure 13:
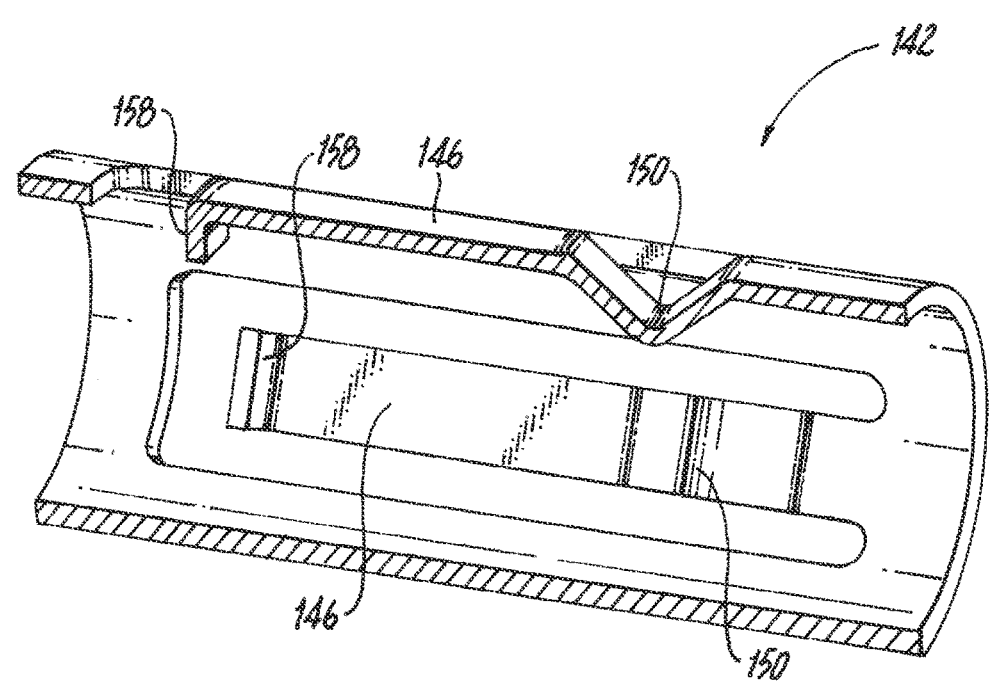
FIG. 13 is a cross-sectional perspective view of the spring tube of FIG. 12, showing inwardly extending flanges of the cantilever arms.

Those skilled in the art will also readily appreciate that an alternate mechanism for torque transmission in device 10 can be used where a distal clip housing 102 includes a diametrical center bar extended across receiving portion to contact the internal flat edges 168 of tines 139 of spring release 136, shown in FIG. 10, that are formed from a slot between tines 139.

Figure 30:
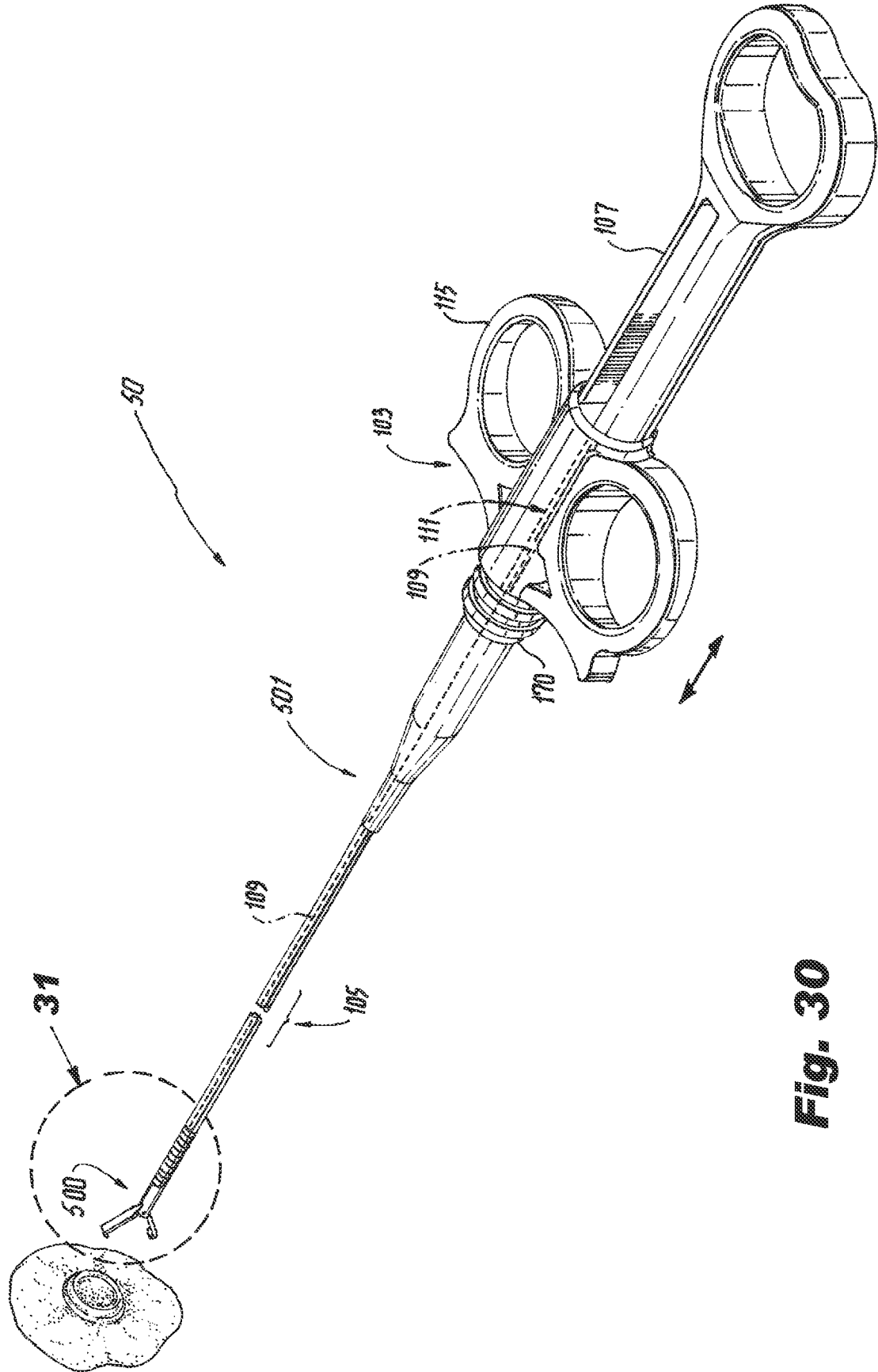
FIG. 30 is a perspective view from the proximal direction of a device for applying a hemostatic clip assembly constructed in accordance with another embodiment of the present disclosure, showing a proximal delivery catheter having a proximal handle assembly and an elongated catheter body and the distal clip assembly.
Figures 31, 32:
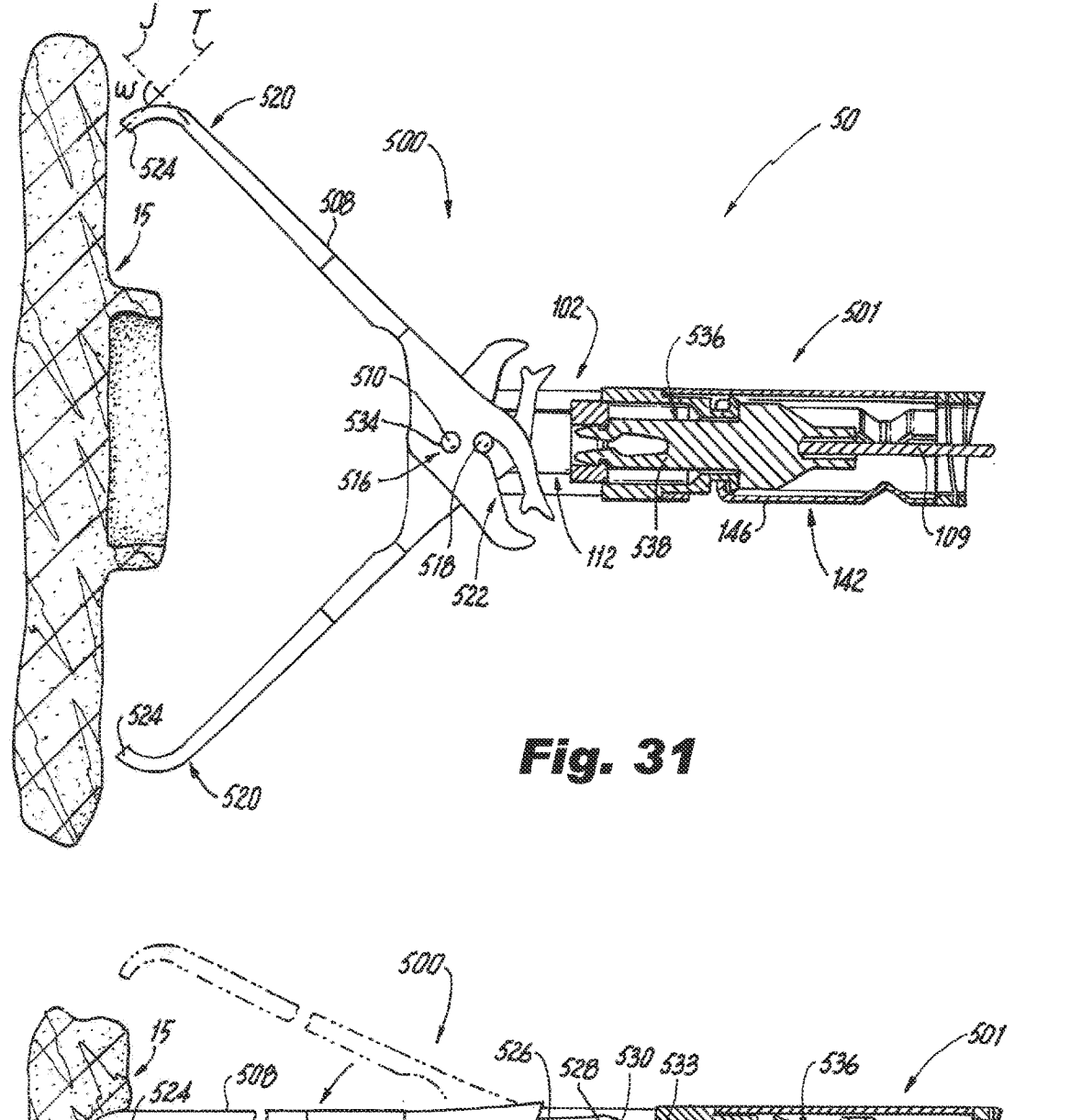
FIG. 31 is a cross-sectional side elevation view of the device of FIG. 30, showing a proximal delivery catheter having a proximal handle assembly and an elongated catheter body and the distal clip assembly having jaw members with a cam slot proximal of a rotation pin, and where the jaw members are shown in an open configuration.
FIG. 32 is a cross-sectional side elevation view of a portion of the device of FIG. 30, showing the jaw members in a closed configuration where the respective distal tips of the jaw members are approximated towards one another to grasp tissue.

As shown in FIGS. 30-31, a surgical device 50 for applying a hemostatic clip assembly 500 includes proximal delivery catheter 501 and the distal clip assembly 500. Delivery catheter 501 of FIG. 30 is the same as delivery catheter 101 shown in FIG. 1 and described above. As such, the description provided above for delivery catheter 101, its proximal handle assembly 103, elongated catheter body 105, drive wire 109, actuation portion 115, grasping portion 107, and the like readily apply to delivery catheter 101 of FIG. 30. The distal clip assembly 500, e.g., a hemostasis clip, separates from the delivery catheter 501 to function as a short-term implant to stop and prevent re-bleeding, or in procedures such as ampullectomy, polypectomy, tissue repair and correction of other tissue defects. Such procedures are the same as those described above in the context of FIG. 1.

As with delivery catheter 101 described above, the proximal delivery catheter 501 of FIGS. 30-31 includes a spring tube 142 coupled to the distal end 143 of the catheter body via weld, adhesive, or other means, the same as described above for spring tube 142. Spring tube 142 of device 50 is the same as spring tube 142 of device 10. Surgical device 50 varies from surgical device 10 in that jaw assembly 504 of distal clip assembly 500 is different from jaw assembly 104 of distal clip assembly 100. Distal clip assembly 500 includes a distal clip housing 102 (which is the same as distal clip housing 102 of assembly 100) and jaw assembly 504 pivotally connected to the distal clip housing 102. The jaw assembly 504 has a pair of cooperating jaw members 508 fixed to the distal clip housing 102 by a first pin 510. The first pin 510 is oriented orthogonally relative to the longitudinal axis A. The hemostatic clip assembly 500 is removably connected to a distal end 143 of the elongated catheter body 105 via the spring tube 142. The proximal delivery catheter 101 is configured and adapted to transmit linear motion along the longitudinal axis A and torsion about the longitudinal axis A to at least a portion of the distal clip assembly 500.

With reference now to FIGS. 31-34, the distal clip assembly 500 includes a jaw adapter yoke 106, which is the same as jaw adapter yoke 106 of distal clip assembly 100 shown in FIGS. 6-7 and described above. The distal clip assembly 500 includes a second pin 518 connecting between the jaw members 508 and the jaw adapter yoke 106. The proximal delivery catheter 101 includes a spring release 536, which essentially the same as spring release 136, described above and shown in FIGS. 10-11, except for some dimensional differences. For example, the proportion of tines 539 of spring release 536 relative to the remainder of spring release 536 is different than that of tines 139. Additionally, spring release 536 includes an outwardly extending flange portion 552, which is slightly different than flange 152 of spring release 136. Outwardly extending flange portion 552 of spring release 536 has a more elongated less-steep slope than flange portion 152 and is positioned such that the flange portion 552 does not deflect cantilever arms 146 of spring tube 142 until locking of pin 518 has been completed. Between the outwardly extending flange portion 552 and a proximal terminal end 519 of the spring release 536 is a continuous constant diameter portion 554, which is the same as continuous constant diameter portion 154. The invention will present a novel deployment mechanism for a hemostatic clip. The novel design allows for a shorter deployed clip body and proposes an improved disconnecting feature.

Figure 33:
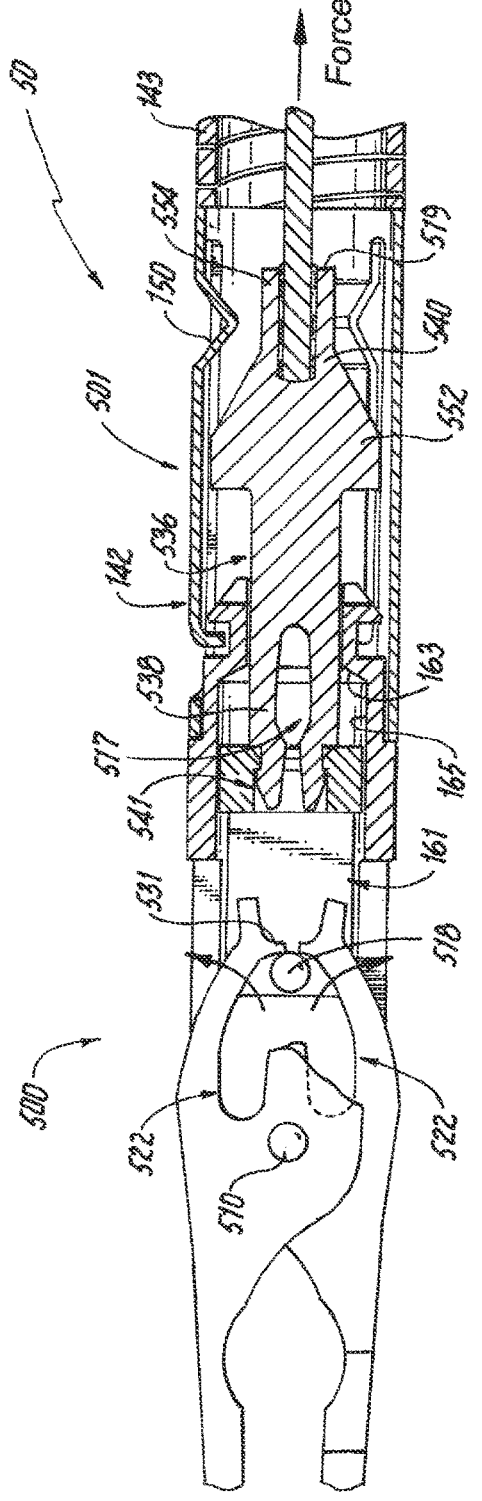
FIG. 33 is a cross-sectional side elevation view of a portion of the device of FIG. 30, schematically showing the transition of the second pin to a locked position within the cam slot.
Figure 34:
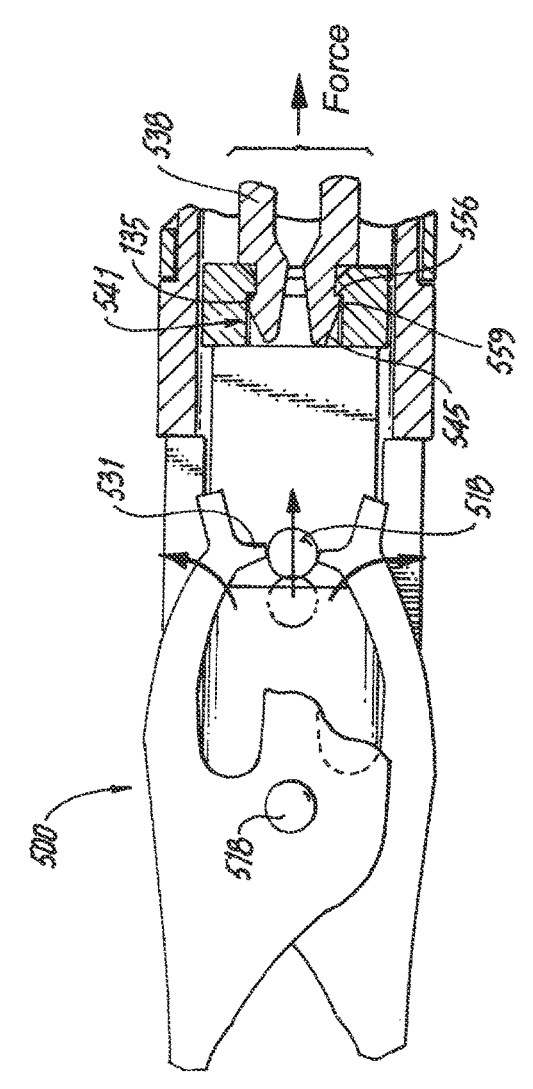
FIG. 34 is a cross-sectional side elevation detail view of a portion of the device of FIG. 30, schematically showing the transition of the second pin to a locked position within the cam slot.

As shown in FIGS. 33-34, spring release 536 has a distal portion 538 configured and adapted to be received within a proximal receiving portion 133 of the jaw adapter yoke 106. The tines 539 form snap feature 541 at the distal most tip of each tine 539. The snap feature 541 includes a tapered outer diameter surface 545 at the distal tip of each tine 539 and an annular mating surface 556 selectively engageable with an inner surface 135 of the receiving portion 133 of the jaw adapter yoke 106. The inner axially facing surface 135 mates with a snap feature 541 (the same as snap feature 141) at axially facing mating surface 556 the distal portion 538 of spring release 536, allowing linear force transmission up to a predetermined value.

With continued reference to FIGS. 33-34, drive wire 109 is mechanically coupled to a proximal portion 540 of the spring release 536, in the same manner as drive wire 109 and spring release 136, to transmit linear and rotational motion from the drive wire 109 to the jaw adapter yoke 106. Friction due to an interference fit between an inside surface 129 of yoke 106 and an outside surface 559 of spring release 536 allows torque transmission from drive wire 109 to the distal subassembly. The distal portion 538 of the spring release 536 is configured and adapted to transmit axial and rotational force to the jaw adapter yoke 106. Tines 539 define a slot 517 therebetween. Annular mating surface 556 allows linear force transmission up to a predetermined value. Different deployment forces can be easily achieved by varying dimensions spring release 536 and/or the diameter of the annular mating surface 556, in a similar manner as described above for spring release 136.

Figures 35, 36:
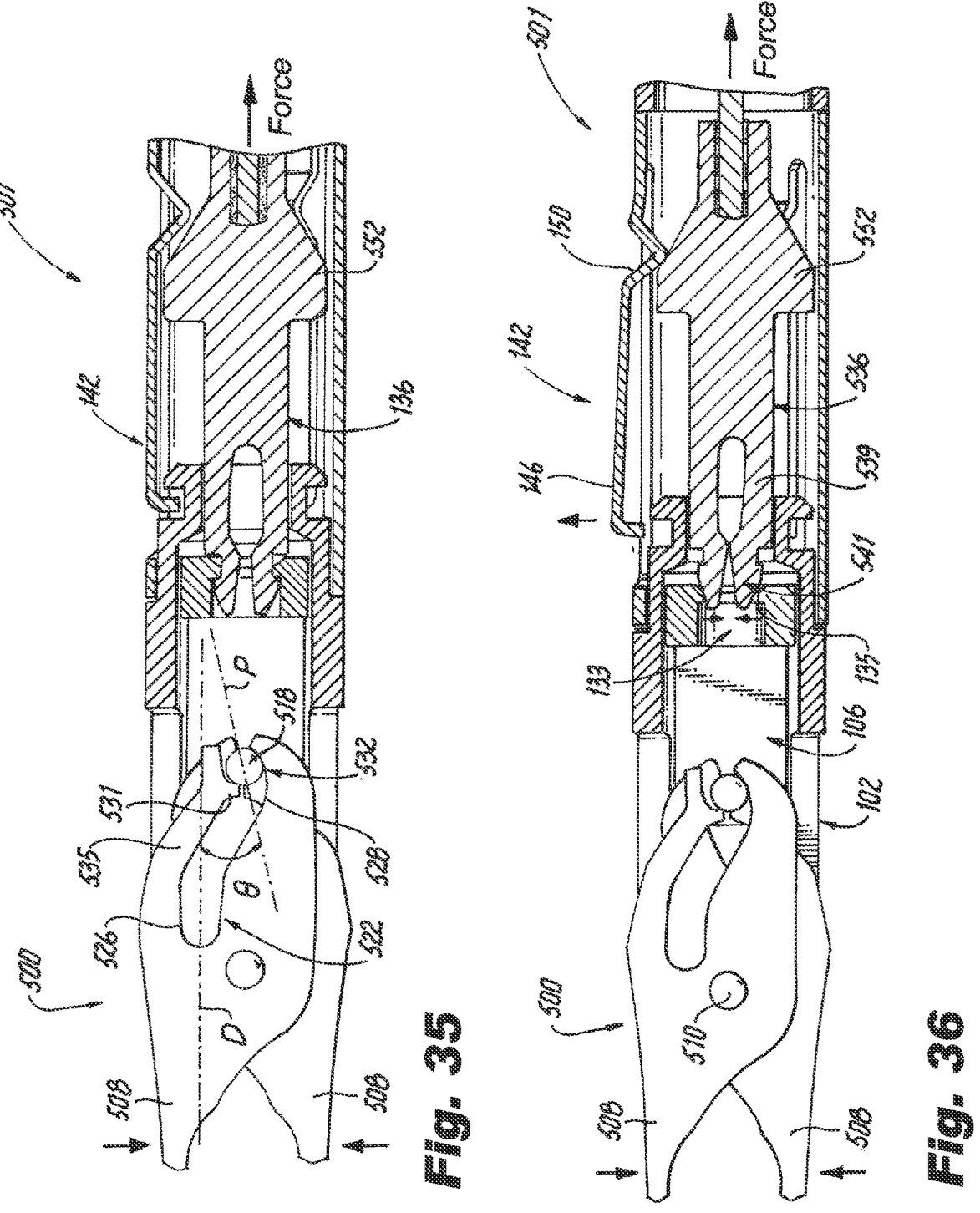
FIG. 35 is a cross-sectional side elevation detail view of a portion of the device of FIG. 30, showing the jaw members in a locked configuration before firing.
FIG. 36 is a cross-sectional side elevation detail view of a portion of the device of FIG. 30, showing the release of the spring release from the jaw adapter yoke and the release of the spring tube from the distal clip housing when firing the device.

With reference to FIGS. 31-35, the jaw members 508 are configured and adapted to rotate about the first pin 510 between an open configuration and a closed configuration, and/or between the closed configuration and the open configuration. Each jaw member 508 includes a proximal body portion 516 and a distal end effector 520. The proximal body portion 516 of each jaw member 508 includes a respective cam slot 522 configured and adapted to receive the second pin 518. Jaw members 508 are driven by the second pin 518, e.g., a cam pin, moving along the cam slots 522 of the jaw members 508. The second pin 518 is configured and adapted to translate within the cam slots 522 to move axially relative to the distal clip housing 102 and the jaw assembly 504 to move the jaw members 508 between the open configuration (FIG. 31) where respective distal tips 524 of the jaw members 508 are moved away from one another, the closed configuration where the respective distal tips 524 of the jaw members 108 are approximated towards one another to grasp tissue (FIG. 32), and a locked configuration (FIG. 35).

With continued reference to FIGS. 31-35, each jaw member 508 includes a pivot aperture 534 configured and adapted to receive the first pin 510. Each jaw member 508 of the jaw assembly 504 is identical to the other member 508, allowing additional economy of scale. The distal end effectors 520 of each jaw member 508 can include at least one pointed peak, multiple peaks, of different or similar size at their distal tips 124. Distal end effectors 520 could also terminate in a combination of pointed peaks and rounded peaks to balance tissue pressure, allowing jaw members 508 to hook tissue with at least one peak and provide atraumatic contact with at least one peak. As shown in FIG. 31, the tooth (or teeth, peaks, etc.) may create an angle ω relative to an axis J of their respective jaw arms 508 between zero and 180 degrees, optimizing the approach angle of distal tips 524 relative to tissue surface. In the embodiment of FIG. 31, the angle ω of a tip axis T relative to axis J is approximately 90 degrees. It is contemplated, however, that the angle ω could be at 0 degrees, such that the tip simply extends from axis J, it could be at 45 degrees, or 180 degrees, where the tip is hooked around such that the tip direction is parallel to axis J. The angle and design of jaw members 508 will be optimized for single jaw tissue retention force during manipulation or tissue apposition. The distance between the pivot aperture 534 and the cam slot 522 dictate the moment arm that translates axial translation to jaw rotation/actuation.

As shown in FIGS. 32-35, each cam slot 522 defines a distal portion 526 and a proximal portion 528, wherein the proximal portion 528 of each cam slot 522 is angled relative to the distal portion 526 of each cam slot 122. The proximal portion 528 of each cam slot 522 defines a proximal axis P extending in a first direction. The distal portion 526 of each cam slot 122 defines a distal axis D extending at an oblique angle θ relative to the proximal axis P, and the distal axes D of each cam slot 522 are positioned at opposite angles relative to one another. The angle of a respective distal axis D relative to proximal axis P can be fine-tuned to provide optimal tissue clamping force given a user's maximum acceptable input force.

With continued reference to FIGS. 32-35, each cam slot 522 includes a proximal locking neck 530, e.g., a locking feature, projecting into the cam slot 522 defining a proximal locking area 532. The jaw members 508 are in the locked configuration when the second pin 518 is proximal relative to the proximal locking neck 530 in the proximal locking area 532. The proximal locking neck 530 includes a protrusion 531 projecting into the cam slot 522. Lock protrusion 531, e.g., a detent, creates a narrowing of cam slot 522 to form the proximal locking neck 530 that interferes with the outer diameter of the second pin 518 as it moves axially in the proximal direction. The continued axial translation of pin 518, as shown in FIGS. 33-34, forces a widening of the cam slot 522 in an elastic manner and creates an additional resistance force on the internal drivetrain, e.g., spring release 536 and spring tube 142. The proximal portion 528 of each cam slot 522 terminates in a rear opening 533. Rear opening 533 is oriented along the proximal axis P, which when in the closed configuration, is generally oblique to the longitudinal axis A. This rear opening 533 creates proximal cantilever jaw arms 535 and 585. In this case, cantilever jaw arm 535, e.g. cantilever lock arm 535, is defined in part by the wall of cam slot 522 having the lock protrusion 531. On a given jaw member 508, cantilever jaw arm 585 is opposite from cantilever lock arm 585 across cam slot 522. Cantilever lock arm 535 results in a decreased force required to lock the clip, and results in a higher rate of successful locking in instances where the jaw members 508 are not perfectly parallel to each other, as deflection in the cantilever lock arm 535 can accommodate some axis offset of the jaw members 508 (further described in the context of FIG. 38, below). Once the second pin 518 crests the inflection point on the protrusion 531, the elastic recovery of cantilever lock arm 535 snaps pin 518 into place behind the protrusion 531, effectively locking the jaws in a closed position. The shape of lock protrusion can vary and can be an arcuate, triangular, or slanted feature. Lock protrusion 531 may also be achieved by reversing the slope of cam slot 522 such that it inflects passed the 0-degree orientation with respect to the axis A of the catheter, described in more detail below.

As shown in FIGS. 6-7 and 31-35, arms 113 of yoke 106 form a slot 161 therebetween. The slot 161 allows the proximal portions 116 of the jaw members 508 rotate around first pin 510. The proximal receiving portion 133 of the jaw adapter yoke 106 mates with snap feature 541 (in the same manner as described above for snap feature 141, above) on the distal portion 538 of spring release 536, allowing linear force transmission up to a predetermined value.

As shown in FIGS. 8-9 and 31-35, spaced apart arms 112 are configured and adapted to provide clearance for respective proximal portions 516 of the jaw members 508 to rotate relative the first pin 510. The distal clip housing 102 connects via a snap fit connection to the spring tube 142, in the same manner as describe above for device 10. The transverse hole 147 of distal clip housing 102 accepts the first pin 510, e.g., the pivot pin, which couples to jaw members 508. As shown in FIG. 33, the inner diameter surface 165 of distal clip housing 102 allows for axial transmission of jaw adapter yoke 106, until jaw adapter yoke 106 contacts the hard stop created by distal facing stop surface 163.

With reference now to FIGS. 31-36, the distal portion 538 of the spring release 536 is configured and adapted to be received within the proximal receiving portion 533 of the jaw adapter yoke 106 and released therefrom, in the same manner as spring release 136 is configured and adapted to be received and released by jaw adapter yoke 106, as described above. The spring release 536 interacts with the spring tube 142 to release the spring tube from the distal clip housing 102 in the same manner as described above for spring release 136 for device 10.

With reference now to FIGS. 32-37, some of the various configurations of device 50 are shown. In FIG. 32, the device 50 is in a closed configuration and the second pin 518 is translated in a more proximal position within each cam slot 522 relative to the open configuration, but second pin 518 is still distal of the locking neck 530 and the protrusion 531. In the closed configuration, the respective distal tips 524 of the jaw members 508 are approximated towards one another to grasp tissue 15 (but not necessarily in abutment with one another). In FIG. 35, the device 50 is in a locked configuration and the second pin 518 is in a proximal position relative to the locking necks 530 and their respective protrusions 531. In the locked configuration, the second pin 518 is within the proximal locking area 532 of each cam slot 522.

Figure 37:
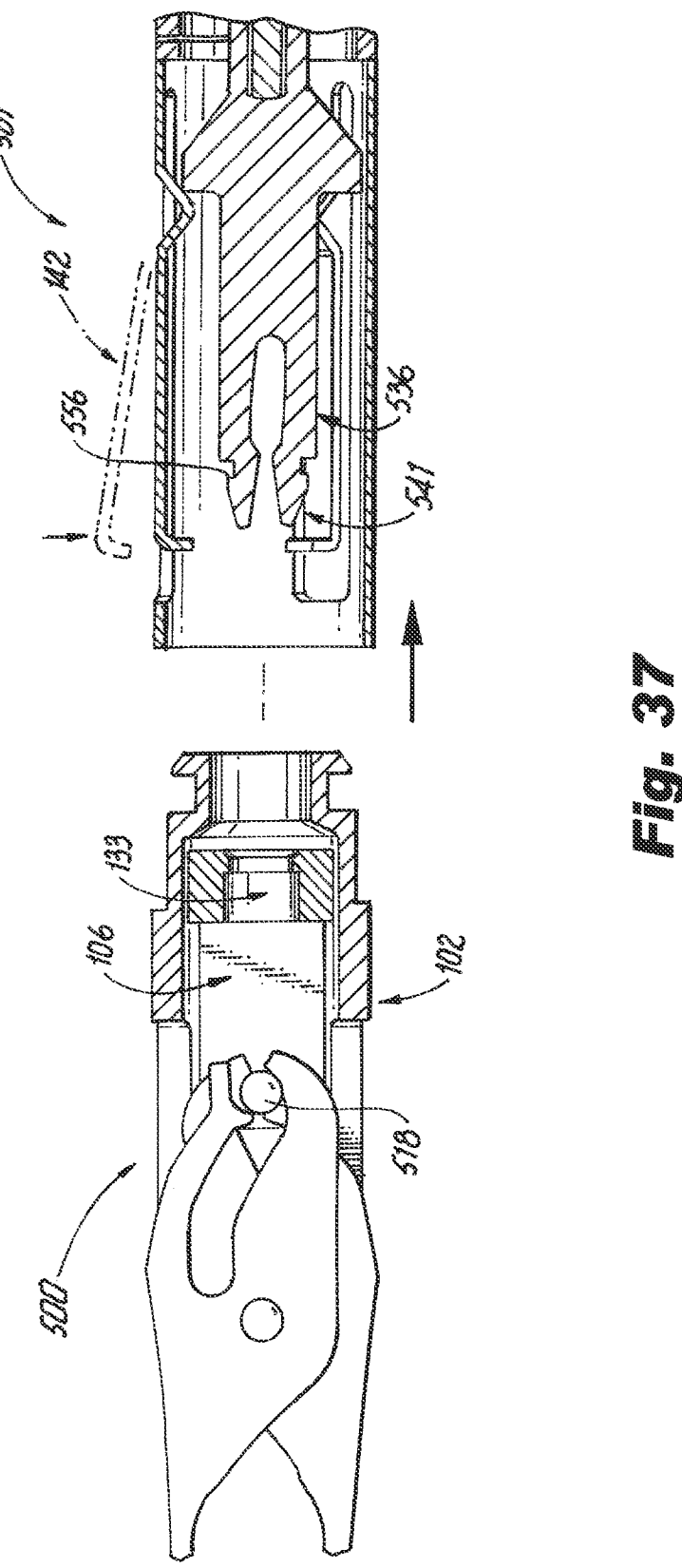
FIG. 37 is a cross-sectional side elevation detail view of a portion of the device of FIG. 30, showing the spring release disconnecting from the jaw adapter yoke for removal of the proximal delivery catheter.

As shown in FIGS. 36-37, once the second pin 518 is in the proximal locking area 532, further axial movement of the spring release 136 in a proximal direction (e.g., away from the tissue 15) acts to "fire" the distal clip assembly 500 by releasing the distal clip assembly 500 from the proximal delivery catheter 101. The further linear motion of the spring release 536 in the proximal direction puts the spring release 536 in tension against jaw adapter yoke 106 due to abutment between mating surface 556 of the snap feature 541 and the inner surface 135 of the receiving portion 133. This tension causes each tine 539 to act as a spring and deflect inwardly, shown schematically by the inwardly pointing arrows in FIG. 36, and release from the receiving portion 133. The release force required to detach spring release 536 from the adapter yoke 106 can be tuned as described above for device 10. In the same way as spring release 136 of device 10, as the spring release 536 moves proximally relative to the jaw adapter yoke 106, it also moves proximally relative to the spring tube 142, causing each cantilever arm 146 to deflect radially outward and disengage from the distal clip housing 102. Full disengagement (e.g., "firing") of the distal clip assembly 500 is realized through both the inward deflection of the tines 539 of spring release 536 and the outward deflection of the cantilever arms 146 of spring tube 142. The user feedback resulting after the firing is a sudden reduction in force required on actuator 115. After firing, release 536 is configured and adapted to then recede into catheter body 105 without further force or feedback. Contrary to some designs seen in the prior art, this gives the user a definitive tactile feedback by way of a sudden reduction in force (from the firing) and allows the handle to displace far past its normal operation longitudinal stroke without resistance, reducing the chance that a user will mistake the retraction of spring release 536 with firing. Both of these factors aid the user in determining successful deployment of distal clip assembly 500. As shown in FIG. 37, after firing, proximal delivery catheter 501 can then be removed from the surgical site, leaving the distal clip assembly 500 to function as a short-term implant.

As shown in FIG. 38, distal clip assembly 500 is shown with jaw members 508 in a locking configuration where the locking angle σ of the jaw members 508 relative to the longitudinal axis A (pre- and post-lock) is 20 degrees. This configuration is encountered when the tissue 15 caught between jaw members 508 forces a larger locking angle. In this case, the respective cantilever lock arms 535 of each jaw member 508 deflect and bend relative to the opposing cantilever jaw arm 585, represented by angle σ, and the remainder of their respective jaw member, e.g. the remainder of proximal body portion 516. As such, in the locked configuration (shown in FIG. 38, which could be pre- or post-firing), an angular distance between respective distal tips 520 of the jaw members and the longitudinal axis is substantially the same as angle σ and ranges from 0 to 20 degrees. This allows the distal clip assembly 500 to accommodate some axis offset of the jaw members 508, results in decreased force required to lock the clip, and results in a higher rate of successful locking in instances where the jaw members 508 are not perfectly parallel to each other. Deflection in the cantilever lock arm 535 accommodates some axis offset of the jaw members 508 (as shown by angle σ), while pin 518 is still locked behind locking protrusions 531.

A method for firing a hemostatic clip assembly, e.g., distal clip assembly 500, includes positioning the distal clip assembly proximate to a target location, e.g., near tissue as shown in FIG. 31, and translating an actuation portion, e.g., actuation portion 115, of a proximal handle assembly, e.g., proximal handle assembly 103, of a proximal delivery catheter, e.g., proximal delivery catheter 101, relative to a grasping portion, e.g., grasping portion 107, of the proximal handle assembly in at least one of a proximal direction or a distal direction. The actuation portion is operatively connected to a jaw adapter yoke, e.g., jaw adapter yoke 106, via a drive wire, e.g., drive wire 109, and a spring release, e.g., spring release 536 to transmit linear motion to the jaw adapter yoke. The linear motion of the jaw adapter yoke transmits the linear motion to a second pin, e.g., second pin 518, positioned within a cam slot, e.g., cam slot 522, of at least one jaw member, e.g., jaw members 508, thereby rotating at least one of the jaw members about the first pin between an open configuration and a closed configuration.

The method includes translating the actuation portion in the proximal direction to transmit the linear motion in the proximal direction to the second pin, as shown in FIG. 33-34, to lock the second pin, as shown behind a lock protrusion, e.g., lock protrusion 531, of the cam slot to lock at least one of the jaw members in a locked configuration, as shown in FIG. 35. Translating the actuation portion includes translating the actuation portion further in the proximal direction to transmit further linear motion in the proximal direction to the spring release, as shown in FIG. 36. The further linear motion in a proximal direction de-coupling a distal portion, e.g., distal portion 538, of the spring release from a receiving portion, e.g., receiving portion 133, of the jaw adapter yoke, as shown in FIG. 36, and causes each cantilever arm, e.g., cantilever arm 146, to deflect radially outward and disengage from the distal clip housing 102.

The methods and systems of the present disclosure, as described above and shown in the drawings, provide for a surgical device with superior properties including simplified user feedback, reduced accidental deployment of the clip assembly and a shorter clip body. Additionally, the firing mechanism is elastic, and permanent deformation, e.g., breakage, is not required to deploy the clip assembly. While the apparatus and methods of the subject disclosure have been showing and described with reference to embodiments, those skilled in the art will readily appreciate that changes and/or modifications may be made thereto without departing from the spirit and score of the subject disclosure.

What is claimed is:

1. A device for applying a hemostatic clip assembly, the device comprising:
    a proximal delivery catheter including a proximal handle assembly and an elongated catheter body extending distally from the proximal handle assembly, the elongated catheter body defining a longitudinal axis; and
    a distal clip assembly removably connected to a distal end of the elongated catheter body, the distal clip assembly including a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein the proximal delivery catheter is configured and adapted to transmit linear motion along the longitudinal axis and torsion about the longitudinal axis to at least a portion of the distal clip assembly, wherein at least one of the jaw members is configured and adapted to rotate about the first pin and to rotate about the longitudinal axis, wherein each jaw member includes a proximal body portion and a distal end effector, wherein the proximal body portion of each jaw member includes a respective cam slot and a rear opening connected to the cam slot and defining at least one proximal cantilever jaw arm, and wherein the distal clip assembly includes a second pin connecting between the jaw members and the jaw adapter yoke, wherein the proximal body portion of each jaw member includes a pivot aperture configured and adapted to receive the first pin, and wherein each respective cam slot is configured and adapted to receive the second pin.

2. The device as recited in claim 1, wherein the distal clip housing includes a pair of spaced apart arms defining a slot configured and adapted to provide clearance for respective proximal portions of the jaw members to rotate relative the first pin.

3. The device as recited in claim 1, wherein the second pin is configured and adapted to translate within the cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration.

4. The device as recited in claim 1, wherein each cam slot includes a proximal locking neck projecting into the cam slot defining a proximal locking area, wherein the jaw members are in the locked configuration when the second pin is proximal relative to the proximal locking neck in the proximal locking area.

5. The device as recited in claim 4, wherein the proximal locking neck includes at least one of a protrusion projecting into the cam slot or a tapered portion.

6. The device as recited in claim 1, wherein the jaw adapter yoke includes a proximal receiving portion and the proximal delivery catheter includes a spring release having a distal portion configured and adapted to be received within the proximal receiving portion of the jaw adapter yoke to transmit axial and rotational force to the jaw adapter yoke, wherein a portion of the spring release between a terminal distal end of the spring release and the outwardly extending flange portion has a constant diameter.

7. The device as recited in claim 1, wherein the proximal delivery catheter includes a spring tube between a proximal end of the distal clip assembly and a distal end of the catheter body.

8. The device as recited in claim 7, wherein the spring tube includes at least one cantilever arm removably coupled to the distal clip housing.

9. The device as recited in claim 8, wherein the at least one cantilever arm includes an inwardly extending flange that removably engages with a circumferential slot defined about a periphery of a proximal end of the distal clip housing.

10. The device as recited in claim 9, wherein the proximal delivery catheter includes a spring release positioned at least partially within the spring tube, wherein the spring tube includes an inward projection, wherein the spring release includes an outwardly extending flange portion configured and adapted to interact with the inward projection of the spring tube to selectively deflect the at least one cantilever arm of the spring tube and release the inwardly extending flange of the at least one cantilever arm from the circumferential slot of the distal clip housing.

11. A hemostatic clip assembly, the assembly comprising:
a distal clip housing defining a longitudinal axis;
a jaw assembly having a pair of cooperating jaw members fixed to the distal clip housing by a first pin, the first pin oriented orthogonally relative to the longitudinal axis, wherein each jaw member includes a proximal body portion and a distal end effector, wherein the proximal body portion of each jaw member includes a respective cam slot and a rear opening connected to the cam slot and defining at least one proximal cantilever jaw arm;
a jaw adapter yoke operatively connected to the jaw members, wherein the jaw adapter yoke is configured and adapted to translate axially along the longitudinal axis and rotate about the longitudinal axis, wherein at least one of the jaw members is configured and adapted to rotate about the first pin and to rotate about the longitudinal axis; and
a second pin connecting between the jaw members and the jaw adapter yoke, wherein each jaw member includes a proximal body portion and a distal end effector, wherein the portion of each jaw member includes a pivot aperture configured and adapted to receive the first pin, and a respective cam slot configured and adapted to receive the second pin.

12. The hemostatic clip assembly as recited in claim 11, wherein the jaw adapter yoke includes a proximal receiving portion configured and adapted to receive therewithin a distal portion of a spring release of a proximal delivery catheter to transmit axial and rotational force to the jaw adapter yoke, wherein a portion of the spring release between a terminal distal end of the spring release and the outwardly extending flange portion has a constant diameter.

13. A hemostatic clip assembly, the assembly comprising:
a distal clip housing defining a longitudinal axis;
a jaw assembly having a pair of cooperating jaw members fixed to the distal clip housing by a first pin, the first pin oriented orthogonally relative to the longitudinal axis, wherein each jaw member includes a proximal body portion and a distal end effector, wherein the proximal body portion of each jaw member includes a respective cam slot and a rear opening connected to the cam slot and defining at least one proximal cantilever jaw arm; and
a jaw adapter yoke operatively connected to the jaw members, wherein the jaw adapter yoke is configured and adapted to translate axially along the longitudinal axis and rotate about the longitudinal axis, wherein at least one of the jaw members is configured and adapted to rotate about the first pin and to rotate about the longitudinal axis,
wherein the jaw adapter yoke includes a proximal receiving portion configured and adapted to receive therewithin a distal portion of a spring release of a proximal delivery catheter to transmit axial and rotational force to the jaw adapter yoke, wherein a portion of the spring release between a terminal distal end of the spring release and the outwardly extending flange portion has a constant diameter.

14. A device for applying a hemostatic clip assembly, the device comprising:
a proximal delivery catheter including a proximal handle assembly and an elongated catheter body extending distally from the proximal handle assembly, the elongated catheter body defining a longitudinal axis; and
a distal clip assembly removably connected to a distal end of the elongated catheter body, the distal clip assembly including a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein the proximal delivery catheter is configured and adapted to transmit linear motion along the longitudinal axis and torsion about the longitudinal axis to at least a portion of the distal clip assembly, wherein at least one of the jaw members is configured and adapted to rotate about the first pin and to rotate about the longitudinal axis, wherein each jaw member includes a proximal body portion and a distal end effector, wherein the proximal body portion of each jaw member includes a respective cam slot and a rear opening connected to the cam slot and defining at least one proximal cantilever jaw arm, and wherein the jaw adapter yoke includes a proximal receiving portion and the proximal delivery catheter includes a spring release having a distal portion configured and adapted to be received within the proximal receiving portion of the jaw adapter yoke to transmit axial and rotational force to the jaw adapter yoke, wherein a portion of the spring release between a terminal distal end of the spring release and the outwardly extending flange portion has a constant diameter.

15. The device as recited in claim 8, wherein the proximal delivery catheter includes a drive wire coupled to a proximal portion of the spring release to transmit linear and rotational motion from the drive wire to the jaw adapter yoke.

16. The device as recited in claim 15, wherein the proximal handle assembly includes an actuation portion coupled to a proximal end of the drive wire, and a grasping portion, wherein the actuation portion is configured and adapted to translate relative to the grasping portion to apply axial force to the drive wire.

17. The device as recited in claim 14, wherein the proximal delivery catheter includes a spring tube between a proximal end of the distal clip assembly and a distal end of the catheter body, wherein the spring tube includes at least one cantilever arm removably coupled to the distal clip housing, wherein the at least one cantilever arm includes an inwardly extending flange that removably engages with a circumferential slot defined about a periphery of a proximal end of the distal clip housing, and wherein the proximal delivery catheter includes a spring release positioned at least partially within the spring tube, wherein the spring tube includes an inward projection, wherein the spring release includes an outwardly extending flange portion configured and adapted to interact with the inward projection of the spring tube to selectively deflect the at least one cantilever arm of the spring tube and release the inwardly extending flange of the at least one cantilever arm from the circumferential slot of the distal clip housing.

18. The device as recited in claim 17, wherein the distal clip assembly includes a second pin connecting between the jaw members and the jaw adapter yoke, wherein the proximal body portion of each jaw member includes a pivot aperture configured and adapted to receive the first pin, and wherein each respective cam slot is configured and adapted to receive the second pin.

19. A device for applying a hemostatic clip assembly, the device comprising:

a proximal delivery catheter including a proximal handle assembly and an elongated catheter body extending distally from the proximal handle assembly, the elongated catheter body defining a longitudinal axis; and a distal clip assembly removably connected to a distal end of the elongated catheter body, the distal clip assembly including a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein the proximal delivery catheter is configured and adapted to transmit linear motion along the longitudinal axis and torsion about the longitudinal axis to at least a portion of the distal clip assembly, wherein at least one of the jaw members is configured and adapted to rotate about the first pin and to rotate about the longitudinal axis, wherein each jaw member includes a proximal body portion and a distal end effector, wherein the proximal body portion of each jaw member includes a respective cam slot and a rear opening connected to the cam slot and defining at least one proximal cantilever jaw arm, wherein the proximal delivery catheter includes a spring tube between a proximal end of the distal clip assembly and a distal end of the catheter body, wherein the spring tube includes at least one cantilever arm removably coupled to the distal clip housing, wherein the at least one cantilever arm includes an inwardly extending flange that removably engages with a circumferential slot defined about a periphery of a proximal end of the distal clip housing, and wherein the proximal delivery catheter includes a spring release positioned at least partially within the spring tube, wherein the spring tube includes an inward projection, wherein the spring release includes an outwardly extending flange portion configured and adapted to interact with the inward projection of the spring tube to selectively deflect the at least one cantilever arm of the spring tube and release the inwardly extending flange of the at least one cantilever arm from the circumferential slot of the distal clip housing.

20. The device as recited in claim 19, wherein the spring release includes a distal portion configured and adapted to be received within a receiving portion of the jaw adapter yoke to transmit linear and rotational motion to the jaw adapter yoke.

21. The device as recited in claim 20, wherein the distal portion of the spring release is divided into at least two tines, wherein each tine has a mating surface selectively engageable with an inner surface of the receiving portion of the jaw adapter yoke.

22. The device as recited in claim 21, wherein each tine is configured and adapted to deflect inwardly and release from the receiving portion when an axial force in a proximal direction is applied to the spring release.

* * * * *